United States Patent
Carra et al.

(10) Patent No.: US 9,708,342 B2
(45) Date of Patent: Jul. 18, 2017

(54) SODIUM (2R,5S,13AR)-7,9-DIOXO-10-((2,4,6-TRIFLUOROBENZYL)CARBAMOYL)-2,3,4,5,7,9,13,13A-OCTAHYDRO-2,5-METHANOPYRIDO[1',2':4,5]PYRAZINO[2,1-B][1, 3]OXAZEPIN-8-OLATE

(71) Applicant: Gilead Sciences, Inc., Foster City, CA (US)

(72) Inventors: Ernest A. Carra, Foster City, CA (US); Irene Chen, San Mateo, CA (US); Vahid Zia, Palo Alto, CA (US)

(73) Assignee: Gilead Sciences, Inc., Foster City, CA (US)

( * ) Notice: Subject to any disclaimer, the term of this patent is extended or adjusted under 35 U.S.C. 154(b) by 0 days.

(21) Appl. No.: 14/744,915

(22) Filed: Jun. 19, 2015

(65) Prior Publication Data

US 2016/0016973 A1  Jan. 21, 2016

Related U.S. Application Data

(60) Provisional application No. 62/015,245, filed on Jun. 20, 2014.

(51) Int. Cl.

| C07D 498/18 | (2006.01) |
|---|---|
| A61K 31/553 | (2006.01) |
| A61K 31/675 | (2006.01) |
| A61K 31/513 | (2006.01) |
| C07D 498/14 | (2006.01) |

(52) U.S. Cl.
CPC .......... *C07D 498/18* (2013.01); *A61K 31/513* (2013.01); *A61K 31/553* (2013.01); *A61K 31/675* (2013.01); *C07D 498/14* (2013.01); *C07B 2200/13* (2013.01)

(58) Field of Classification Search
CPC .. C07D 498/18; A61K 31/553; A61K 31/675; A61K 31/513
USPC .................................. 544/95; 514/81, 229.5
See application file for complete search history.

(56) References Cited

U.S. PATENT DOCUMENTS

| 5,814,639 | A | 9/1998 | Liotta et al. |
|---|---|---|---|
| 5,914,331 | A | 6/1999 | Liotta et al. |
| 5,922,695 | A | 7/1999 | Arimilli et al. |
| 5,935,946 | A | 8/1999 | Munger, Jr. et al. |
| 5,977,089 | A | 11/1999 | Arimilli et al. |
| 6,043,230 | A | 3/2000 | Arimilli et al. |
| 6,620,841 | B1 | 9/2003 | Fujishita et al. |
| 6,642,245 | B1 | 11/2003 | Liotta et al. |
| 6,703,396 | B1 | 3/2004 | Liotta et al. |
| 7,176,220 | B2 | 2/2007 | Satoh et al. |
| 7,419,969 | B2 | 9/2008 | Naidu et al. |
| 7,550,463 | B2 | 6/2009 | Yoshida |
| 7,635,704 | B2 | 12/2009 | Satoh et al. |
| 7,858,788 | B2 | 12/2010 | Yoshida et al. |
| 8,129,385 | B2 | 3/2012 | Johns et al. |
| 8,148,374 | B2 | 4/2012 | Desai et al. |
| 8,188,271 | B2 | 5/2012 | Yoshida et al. |
| 8,410,103 | B2 | 4/2013 | Johns et al. |
| 8,592,397 | B2 | 11/2013 | Dahl et al. |
| 8,633,219 | B2 | 1/2014 | Matsuzaki et al. |
| 8,716,264 | B2 | 5/2014 | Dahl et al. |
| 8,778,943 | B2 | 7/2014 | Johns et al. |
| 8,981,103 | B2 | 3/2015 | Ando et al. |
| 8,987,441 | B2 | 3/2015 | Takahashi et al. |
| 9,051,337 | B2 | 6/2015 | Johns et al. |
| 9,216,996 | B2 | 12/2015 | Jin et al. |
| 2005/0054645 | A1 | 3/2005 | Miyazaki et al. |
| 2005/0137224 | A1 | 6/2005 | Shima et al. |
| 2006/0086401 | A1 | 4/2006 | Sato |
| 2007/0072831 | A1 | 3/2007 | Cai et al. |
| 2008/0020010 | A1 | 1/2008 | Nair et al. |
| 2008/0139579 | A1 | 6/2008 | Morrissette et al. |
| 2008/0161271 | A1 | 7/2008 | Yoshida et al. |
| 2008/0280945 | A1 | 11/2008 | Lohani et al. |
| 2009/0036684 | A1 | 2/2009 | Matsuda et al. |
| 2009/0143356 | A1 | 6/2009 | Yoshida et al. |
| 2009/0253677 | A1 | 10/2009 | Beaulieu et al. |
| 2009/0318702 | A1 | 12/2009 | Matsuda et al. |
| 2010/0068695 | A1 | 3/2010 | Kiyama et al. |
| 2012/0022251 | A1 | 1/2012 | Sumino et al. |
| 2012/0108564 | A1 | 5/2012 | Miyazaki et al. |
| 2013/0006485 | A1 | 1/2013 | Kwasniewski |
| 2014/0011995 | A1 | 1/2014 | Sumino et al. |
| 2014/0094605 | A1 | 4/2014 | Yoshida et al. |
| 2014/0221355 | A1 | 8/2014 | Lazerwith et al. |
| 2014/0221356 | A1 | 8/2014 | Jin et al. |
| 2014/0221378 | A1 | 8/2014 | Miyazaki et al. |
| 2014/0243521 | A1 | 8/2014 | Yoshida et al. |
| 2014/0256937 | A1 | 9/2014 | Akiyama |
| 2015/0232479 | A1 | 8/2015 | Johns et al. |

FOREIGN PATENT DOCUMENTS

| EP | 154199 | A2 | 9/1985 |
|---|---|---|---|
| EP | 1422218 | A1 | 5/2004 |
| EP | 1544199 | A1 | 6/2005 |
| EP | 1874117 | A1 | 1/2008 |

(Continued)

OTHER PUBLICATIONS

Agrawal, et al. (2012) "Probing Chelation Motifs in HIV Integrase Inhibitors" Proc. Natl. Acad. Sci. U.S.A.; 109(7): 2251-2256.

AIDS treatment Guidelines (2013)—"AIDS info Guidelines for the Use of Antiretroviral Agents in HIV-1-Infected Adults and Adolescents," [downloaded from http://aidsinfo.nih.gov/guidelines on Mar. 15, 2013], 267 pages.

Akiyama, et al. (2013) "Discovery of Novel HIV Integrase Inhibitors Part 2. Selection and Evaluation of an Azabicylic Carbamoyl Pyridone as apre-Clinical Candidate" Poster, American Chemical Society National Meeting and Exposition; Apr. 7-11; New Orleans, LA.

(Continued)

*Primary Examiner* — Kahsay Habte

(57) ABSTRACT

The present invention relates to sodium (2R,5S,13aR)-7,9-dioxo-10-((2,4,6-trifluorobenzyl) carbamoyl)-2,3,4,5,7,9,13,13a-octahydro-2,5-methanopyrido[1',2':4,5]pyrazino[2,1-b][1,3] oxazepin-8-olate Form I and the therapeutic uses thereof.

26 Claims, 7 Drawing Sheets

(56) References Cited

FOREIGN PATENT DOCUMENTS

| | | |
|---|---|---|
| EP | 2412709 A1 | 2/2012 |
| EP | 2465580 A1 | 6/2012 |
| EP | 2527007 A1 | 11/2012 |
| GB | 2345058 A | 6/2000 |
| WO | WO-99/25345 A1 | 5/1999 |
| WO | WO-03030897 A1 | 4/2003 |
| WO | WO-03035077 A1 | 5/2003 |
| WO | WO-2004/004657 A2 | 1/2004 |
| WO | WO-2004/024078 A2 | 3/2004 |
| WO | WO-2005/042533 A2 | 5/2005 |
| WO | WO-2005/074513 A2 | 8/2005 |
| WO | WO-2005/110414 A2 | 11/2005 |
| WO | WO-2005/112930 A1 | 12/2005 |
| WO | WO-2005/113508 A1 | 12/2005 |
| WO | WO-2005/113509 A1 | 12/2005 |
| WO | WO-2007/014352 A2 | 2/2007 |
| WO | WO-2007/079260 A1 | 7/2007 |
| WO | WO-2007/102499 A1 | 9/2007 |
| WO | WO-2007/102512 A1 | 9/2007 |
| WO | WO-2008/002959 A2 | 1/2008 |
| WO | WO-2008/033836 A2 | 3/2008 |
| WO | WO-2008/048538 A1 | 4/2008 |
| WO | WO-2009/006199 A1 | 1/2009 |
| WO | WO-2009/006203 A1 | 1/2009 |
| WO | WO-2009/036161 A1 | 3/2009 |
| WO | WO-2010/011812 A1 | 1/2010 |
| WO | WO-2010/011813 A1 | 1/2010 |
| WO | WO-2012/018065 A1 | 2/2012 |
| WO | WO-2012/151361 A1 | 11/2012 |
| WO | WO-2012/151567 A1 | 11/2012 |
| WO | WO-2013/038407 A1 | 3/2013 |
| WO | WO-2014/022707 A1 | 2/2014 |
| WO | WO-2014/093941 A1 | 6/2014 |
| WO | WO-2014/100077 A1 | 6/2014 |
| WO | WO-2014/100323 A1 | 6/2014 |

OTHER PUBLICATIONS

Andrews, C. et al. (2014) "Long-Acting Integrase Inhibitor Protects Macaques from Intrarectal Simian/Human Immunodeficiency Virus," Science 343:1151-1154.

Bisel, P. et al. (1998) "Diastereoselective .alpha.-iminoamine rearrangement: asymmetric synthesis of (R)-(−)- and (S)-(−)-2-benzyl-2-hydroxycyclohexanone" Tetrahedron: Asymmetry 9:4027-4034.

Brehm et. al. (1954) "The Relative Acidifying Influence of Oxygen and Sulfur Atoms on α-Hydrogen Atoms" 76:5389-5391.

Brinson, C. et al. (2013) "Dolutegravir Treatment Response and Safety by Key Subgroups in Treatment Naive HIV Infected Individuals" Poster, 20th Conference on Retroviruses and Opportunistic Infections; Mar. 3-6, 2013; Atlanta, GA.

Cahn, P. et al. (2013) "Dolutegravir (DTG) is Superior to Raltegravir (RAL) in ART-Experienced, Integrase-Naive Subjects: Week 48 Results From Sailing (ING111762)" Presentation, 7.sup.th IAS Conference on HIV Pathogenesis, Treatment and Prevention;Jun. 30-Jul. 3; Kuala Lumpur, Malaysia.

Canducci, F. et al. (2013) "In vitro phenotypes to elvitegravir and dolutegravir in primary macrophages and lymphocytes of clonal recombinant viral variants selected in patients failing raltegravir", J Antimicrob Chemother., 68:2525-32.

Castagna, A. et al. (2014) "Dolutegravir in Antiretroviral-Experienced Patients With Raltegravir- and/or Elvitegravir-Resistant HIV-1: 24-Week Results of the Phase III VIKING-3 Study" Infectious Diseases Society of America Journal of InfectiousDiseases 210:354-62.

Castellino, S., et al., (2013), "Metabolism, Excretion, and Mass Balance of the HIV-1 Integrase Inhibitor Dolutegravir in Humans", Antimicrobial Agents and Chemother., 57:3536-46.

Chen, D. et al. (2003) "New C19-diterpenoid alkaloids from the roots of Aconitum transsecutum" Abstract, Huaxue Xuebao 61(6):901-906.

Chen, S. et al. (2014) "Evaluation of the effect of UGT1A1 polymorphisms on dolutegravir pharmacokinetics" Pharmacogenomics, 15(1):9-16.

Clotet, G. et al. (2014) "Once-daily dolutegravir versus darunavir plus ritonavir in antiretroviral-naive adults with HIV-1 infection (FLAMINGO) 48 week results from the randomised open-label phase 3b study", Lancet, 383:2222-31.

Cohen, J. et al. (2014) "A Bid to Thwart HIV With Shot of Long-Lasting Drug" Science 343:1067.

Cottrell, M. et al. (2013) "Clinical Pharmacokinetic, Pharmacodynamic and Drug-Interaction Profile of the Integrase Inhibitor Dolutegravir" Clin Pharmacokinet 52:981-994.

Culp, A. et al. (2014) "Metabolism, Excretion, and Mass Balance of the HIV Integrase Inhibitor, Cabotegravir (GSK1265744) in Humans" Presentation, 54th Intersience Conference on Antimicrobial Agents and Chemotherapy; Sep. 5-9; Washington, DC., 1-7.

Curtis, L. et al. (2013) "Once-Daily Dolutegravir (DTG; GSK1349572) Has a Renal Safety Profile Comparable to Raltegravir (RAL) and Efavirenz in Antiretroviral (ART)-Naive Adults: 48 Week Results From SPRING-2 (ING113086) and SINGLE (ING114467)" Poster No. CUPE 282, 7.sup.th IAS Conference on HIV Pathogenesis, Treatment and Prevention; Jun. 30-Jul. 3; Kuala Lumpur, Malaysia.

Deanda, F. et al. (2013) "Dolutegravir Interactions with HIV-1 Integrase-DNA: Structural Rationale for Drug Resistance and Dissociation Kinetics" PLOS ONE 8(10): e77448 1-12.

Enright, B. et al. (2010) "Assessment of Hydroxypropyl Methylcellulose, Propylene Glycol, Polysorbate 80, and Hydroxypropyl-.beta.-Cyclodextrin for Use in Developmental and Reproductive Toxicology Studies" Birth Defects Research (Part B) 89:504-516.

European Search Report dated Mar. 31, 2015 for EP application No. 13815937.1.

FDA DTG Pharmacology Review—Center for Drug Evaluation and Research; DTG PharmTox Review 2013, 103 pages.

FDA_DDI Guidance for Industry—Drug Interaction Studies—Study Design, Data Analysis, Implications for Dosing, and Labeling Recommendations, 79 pages.

Feinberg, J. et al. (2013) "Once-Daily Dolutegravir (DTG) is Superior to Darunavir/Ritonavir (DRV)/f) in Antiretroviral-Naive Adults: 48 Week Results from FLAMINGO (ING114915)" Presentation, 53.sup.rd ICAAC Interscience Conference on AntimicrobialAgents and Chemotherapy; Sep. 10-13; Denver CO.

Gad, S. et al. (2006) "Nonclinical Vehicle Use in Studies by Multiple Routes in Multiple Species" International Journal of Toxicology 25:499-521.

Gao, Y. et al. (2007) "Attenuating Pregnane X Receptor (PXR Activiatin: A Molecular Modeling Approach" Xenobiotica 37(2):124-138.

Gein, V. L., et al. (1992) "Synthesis of 4-Substituted 1-Methyl-5-Aryl- and 1,5-Diaryltetrahydropyrrole-2,3-Diones and their Antiviral Action" translated from Khimik-farmatsevticheskii Zhumal; 25(12):37-40.

Gould, S. et al. (2005) "2-Hydroxypropyl-.beta.-cyclodextrin (HP-.beta.-CD): A toxicology review" Food and Chemical Toxicology 43:1451-1459.

Gouverneur, V. et al. (1998) "New Acylnitroso Compounds for the Asymmetric Oxyamination of Dienes" Tetrahedron 54:10537-10554.

Grobler, J., et al. (2002) "Diketo Acid Inhibitor Mechanism and HIV-1 Integrase: Implications for Metal Binding in the Active Site of Phosphotransferase Enzymes" Proc. Natl. Acad. Sci. U.S.A.; 99(10):6661-6666.

Guitierez, M., "Drug safety profile of integrase strand transfer inhibitors," Expert Opin. Drug Saf. (2014) 13(4):431-445.

Hare, S. et al. (2011) "Structural and Functional Analyses of the Second-Generation Integrase Strand Transfer Inhibitor Dolutegravir (S/GSK1349572)" Molecular Pharmacology 80(4):565-572.

Hightower, K., "Dolutegravir (S/GKS1349572) Exhibits Siginifcantly Slower Dissociation than Raltegrvir and Elvitegravir from Wild-Type and Integrase Inhibitor-Resistant HIV-1 Integrase-DNA Complexes," Antimicrobial Agents and Chemotherapy 55(10):4552-4559 (2011).

(56) References Cited

OTHER PUBLICATIONS

Huang, W. et al. (2014) "Impact of Raltegravir/Elvitegravir Selected Mutationson Dolutegravir Cross-Resistance" Poster 595; 21.sup.st Conference on Retroviruses and Opportunistic Infection; Mar. 3-6; Boston, MA.

Hurt et al., (2014), "Resistance to HIV Integrase Strand Transfer Inhibitors Among Clinical Specimens in the United States, 2009-2012", Clin Infect Dis., 58:423-31.

Hurt, C. et al. (2013) "Characterization of Resistance to Integrase Strand Transfer Inhibitors among Clinical Specimens in the United States, 2009-2012" Poster 591; 20th Conference on Retroviruses and Opportunistic Infections; Mar. 3-6; Atlanta, GA.

International Preliminary Report on Patentability dated Jun. 23, 2015 for PCT/US2013/076367.

Intl Search Report—Written Opinion dated Sep. 18, 2016 for PCT/US2006/016604.

Intl. Search Report—Written Opinion dated Feb. 9, 2016 for PCT/US2015/026017.

Intl. Search Report dated Mar. 12, 2014 for PCT/US2013/076367.

Johns, B. et al., (2013), "HIV Integrase Inhibitors", Successful Strategies for Discovery of Antiviral Drugs, 32(6):149-88.

Johns, B., et al., "Carbamoyl Pyridone HIV⊐1 Integrase Inhibitors 3. A Diastereomeric Approach to Chiral Nonracemic Tricyclic Ring Systems and the Discovery of Dolutegravir (S/GSK1349572) and (S/GSK1265744)," J. Med. Chem. (2013) 56:5901-5916 (16 pages).

Kawasuji, T., et al. (2007) "3-Hydroxy-1,5-dihydro-pyrrol-2-one Derivatives as Advanced Inhibitors of HIV Integrase" Bioorganic & Medicinal Chemistry; 15:5487-5492.

Kawasuji, T., et al. (2012) "Carbamoyl Pyridone HIV-1 Integrase Inhibitors. 1. Molecular Design and Establishment of an Advanced Two-Metal Binding Pharmacophore" J. Med. Chem.; 55(20):8735-8744.

Kliewer, S. et al. (2002) "The Nuclear Pregnane X Receptor: A Key Regulator of Xenobiotic Metabolism" Endocrine Reviews 23(5):687-702.

Kobayashi, M. et al. (2011) "In Vitro Antiretroviral Properties of S/GSK1349572, a Next-Generation HIV Integrase Inhibitor" Antimicrob Agents and Chemother 55(2):813-21.

Krow, G. et al. (2008) "Selectfluor as a Nucleofuge in the Reactions of Azabicyclo[n. 2.1]alkane .beta.-Halocarbamic Acid Esters (n=2,3)" J. Org. Chem. 73:2122-2129.

Lepist, E. et al. (2011) "Effect of Cobicistat and Ritonavir on Proximal Renal Tubular Cell Uptake and Efflux Tansporters" Poster A1-1724; 51.sup.st Interscience Conference on Antimicrobial Agents and Chemotherapy; Sep. 17-20; Chicago, IL.

Letendre, S. et al. (2013) "Distribution and Antiviral Activity in Cerebrospinal Fluid (CSF) of the Integrase Inhibitor, Dolutegravir (DTG): ING116070 Week 16 Results" Poster 178LB; 20th Conference on Retroviruses and Opportunistic Infections; Mar. 3-6; Atlanta, GA.

Lou, Y. et al. (2013) "Meta-Analysis of Safety Data From 8 Clinical Studies With GSK1265744, an HIV Integrase Inhibitor, Dosed Orally or as Injection of Long-Acting Parenteral Nanosuspension (LAP)" Poster H-672; 53rd Interscience Conference onAntimicrobial Agents and Chemotherapy; Sep. 10-13; Denver, CO.

Maggi, P., (2014) "The Problem of Renal Function Monitoring in Patients Treated With the Novel Antiretroviral Drugs", HIV Clinical Trials, HIV Clin Trials;15(3):87-91.

Malet, I., et al., (2014) "New raltegravir resistance pathways induce broad cross-resistance to all currently used integrase inhibitors", J Antimicrob Chemother, 69: 2118-2122.

Margolis et al. (2014) "744 and Rilpivirine As Two Drug Oral Maintenance Therapy: LAI116482 (LATTE) Week 48 Results" Presentation; 21st Conference on Retroviruses and Opportunistic Infections; Mar. 3-6; Boston, MA.

Menendez-Arias, L., Alvarez, M., "Antiretroviral therapy and drug resistance in human immunodeficiency virus type 2 infection," Antiviral Res. (2013), http://dx.doi.org/10.1016/j.antiviral.2013.12.001.

Metifiot, M. et al. (2013) "HIV Integrase Inhibitors: 20-Year Landmark and Challenges" Advances in Pharmacology 67:75-105.

Min, S. et al. (2010) "Pharmacokinetics and Safety of S/GSK1349572, a Next-Generation HIV Integrase Inhibitor, in Healthy Volunteers" Antimicrob Agents and Chemother 54(1):254-258.

Min, S. et al. (2011) "Antiviral activity, safety, and pharmacokinetics/pharmacodynamics of dolutegravir as 10-day monotherapy in HIV-1-infected adults" AIDS 25(14):1737-1745.

Nair, V. et al. (2014) "Pharmacokinetics and Dose-range Finding Toxicity of a Novel anti-HIV Active Integrase Inhibitor" Supplementary Materials.

Nichols, G. et al (2013) "Phase 3 Assessment of Dolutegravir (DTG) 50 mg Twice Daily (BID) in Hiv-1-Infected Subjects With Raltegravir (RAL) and/or Elvitegravir (EVG) Resistance in VIKING-3: Week 24 Results of All 183 Subjects Enrolled" PosterTULBPE19; 7.sup.th IAS Conference on HIV Pathogenesis, Treatment and Prevention Jun. 30-Jul. 3; Kuala Lumpur, Malaysia.

Nichols, G. et al. (2012) "Antiviral Activity of Dolutegravir in Subjects With Failure on an Integrase Inhibitor-Based Regimen: Week 24 Phase 3 Results From VIKING-3" Presentation O232; 11th International Congress on Drug Therapy in HIV Infection; Nov. 11-15; Glasgow, UK.

Nishioka, K. et al. (1992) "C-Labeling of a Tetrahydroacridine, a Novel CNS-Selective Cholinesterase Inhibitor" Journal of Labelled Compounds and Radiopharmaceuticals XXXI(7):553-560.

Office Action dated Mar. 30, 2015 for Pakistan Appl. No. 908/2013.

Opposition Decision in European patent application No. 02749384.0, dated Mar. 12, 2015.

Pace, P., et al. (2007) "Dihydroxypyrimidine-4-carboxamides as Novel Potent and Selective HIV Integrase Inhibitors" J. Med. Chem; 50:2225-2239.

Park, B. et al. (2001) "Metabolism of Fluorine-Containing Drugs" Annu. Rev. Pharmacol. Toxicol. 41:443-70.

Patel, P. et al. (2014) "Relative Bioavailability of a Paediatric Granule Formulation of the HIV Integrase Inhibitor, Dolutegravir, in Healthy Adult Subjects" Antiviral Therapy.

Patel, P., et al., "Pharmacokinetics of the HIV integrase inhibitor S/GSK1349572 co-administered with acid-reducing agents and multivitamins in healthy volunteers," J Antimicrob Chemother (2011); 66: 1567-1572.

Peng, C. et al. (2002) "Norditerpenoid alkaloids from the roots of *Aconitum hemsleyanum* Pritz. var. *pengzhouense*" Abstract, Chinese Chemical Letters 13(3):233-236.

Petrocchi, A., et al. (2007) "From Dihydroxypyrimidine Carboxylic Acids to Carboxamide HIV-1 Integrase Inhibitors: SAR Around the Amide Moiety" Bioorganic & Medicinal Chemistry Letters; 17:350-353.

Huang, W., et al., Poster #595 Impact of Raltegravir/Elvitegravir Selected Mutationson Dolutegravir Cross-Resistance, 21st Conference on Retroviruses and Opportunistic Infection dated Mar. 3-6, 2014, 1 page.

Pozniak, A. et al. (2013) "Dolutegravir (DTG) Versus Raltegravir (RAL) in ART-Experienced, Integrase-Naive Subjects: 24-Week Interim Results from Sailing (ING111762)" Poster 179LB; 20th Conference on Retroviruses and Opportunistic Infections; Mar. 3-6; Atlanta, GA.

Quashie, P. et al. (2013) "Evolution of HIV integrase resistance mutations" Curr Opin Infect Dis 26:43-49.

Raffi et al, "Once-daily dolutegravir versus twice-daily raltegravir in; antiretroviral-naive adults with HIV-1 infection (SPRING-2; study): 96 week results from a randomised, double-blind,; non-inferiority trial," www.thelancet.com/infection vol. 13, pp. 927-935, Published online Nov. 2013.

Raffi et al., . "Once-daily dolutegravir versus raltegravir in antiretroviral-naive adults with HIV-1 infection: 48 week results from the randomised, double-blind, non-inferiority SPRING-2 study," www.thelancet.com Published online Jan. 8, 2013 http://dx.doi.org/10.1016/S0140-6736(12)61853-4, 9 pages.

Raffi_Poster_DTG clinical data summary IAS Kuala Lumpur Jul. 2013 (Spring 2), 1 page.

Ragan, J. et al. (1995) "Studies of the Alkylation of Chiral, Non-Racemic, Tricyclic Pyrrolidinones," Heterocycles 41:57-70.

(56) References Cited

OTHER PUBLICATIONS

Reese, M. et al. (2013) "In Vitro Investigations into the Roles of Drug Transporters and Metabolizing Enzymes in the Disposition and Drug Interactions of Dolutegravir, a HIV Integrase Inhibitor" Drug Metab Dispos 41:353-361.
Rhodes, M., et al., "Assessing a Theoretical Risk of Dolutegravir-Induced Developmental Immunotoxicity in Juvenile Rats," Toxicological Sciences 130(1), 70-81 (2012).
Saag, M.S., (2006), "Emtricitabine, a new antiretroviral agent with activity against HIV and hepatitis B virus", Clin Infect Dis., 42:126-31.
Song, I. et al. (2010) "Lack of Interaction Between the HIV Integrase Inhibitor S/GSK1349572 and Tenofovir in Healthy Subjects" JAIDS 55(3):365-367.
Song, I. et al. (2012) "Effect of Food on the Pharmacokinetics of the Integrase Inhibitor Dolutegravir" Antimicrob Agents and Chemother 56(3):1627-1629.
Song, I. et al. (2013) "Dolutegrvir Has No Effect on the Pharmacokinetics of Methadone or Oral Contraceptives With Norgestimate and Ethinyl Estradiol" Poster 535; 20th Conference on Retroviruses and Opportunistic Infections; Mar. 3-6; Atlanta, GA.
Song, I. et al. (2013) "Pharmacokinetics (PK) and PK.sub.-Pharmacodynamic (PD) Relationship of Dolutegravir (DTG) in Integrase Inhibitor (INI)-Naive Subjects" Poster A-1573; 53rd Interscience Conference on Antimicrobial Agents and Chemotherapy; Sep. 10-13; Denver, CO.
Soriano, V., et al. (2011) "Dolutegravir (GSK/ViiV Integrase) Treatment (with 50mg Once & Twice Daily) of HIV Subjects with Raltegravir Resistance & 3-Class ART Resistance: viral suppression at Week 24 in the VIKING Study" Presentation; EACS; Oct. 12-15; Belgrade, Serbia.
Spreen, W. et al (2013) "First study of repeat dose co-administration of GSK1265744 and TMC278 long-acting parenteral nanosuspensions: pharmacokinetics, safety, and tolerability in healthy adults" Presentation; 7.sup.th IAS Conference on HIVPathogenesis, Treatment and Prevention Jun. 30-Jul. 3; Kuala Lumpur, Malaysia.
Spreen, W. et al. (2012) "Pharmacokinetics, Safety and Tolerability of the HIV Integrase Inhibitor S/GSK1265744 Long Acting Parenteral Nanosuspension Following Single Dose Administration to Healthy Adults" Presentation; 19th International AIDSConference; Jul. 22-27; Washington DC.
Spreen, W. et al. (2013) "Pharmacokinetics, Safety, and Monotherapy Antiviral Activity of GSK1265744, an HIV Integrase Strand Transfer Inhibitor" HIV Clin Trials 14(5):192-203.
Stellbrink, H. et al. (2013) "Dolutegravir in antiretroviral-naive adults with HIV-1: 96-week results from a randomized dose-ranging study" AIDS 27:1771-1778.
Summa, V., et al. (2006) "4,5-Dihydroxpyrimidine Carboxamides and N-Alkyl-5-hydroxypyrimidinone Carboxamides are Potent, Selective HIV Integrase Inhibitors with Good Pharmacokinetic Profiles in Preclinical Species" J. Med. Chem; 49:6646-6649.
Summary of Product Characteristics—Annex I, Leaflet, 62 pages—EU—Triumeq [downloaded Sep. 8, 2014].
Taoda, Y. et al. (2013) "Discovery of Novel HIV Integrase Inhibitors Part 1. Molecular Design and SAR of Azabicyclic Carbamoyl Pyridone Inhibitors" Poster; 245.sup.th American Chemical Society National Meeting and Exposition; Apr. 7-11; New Orleans, LA.
Tchaparian, Eskouhie, "Drug Transporters: An Overview of Their Role in Drug Interactions; Recommended Strategies to Assess Drug Transporters froma Regulatory and Industry Perspective," FDA Guidance Compliance Regulatory Information Guidances (Feb. 14, 2013), 19 pages.
Thackaberry, E. et al. (2010) "Comprehensive Investigation of Hydroxypropyl Methylcellulose, Propylene Glycol, Polysorbate 80, and Hydroxypropyl-Beta-Cyclodextrin for use in General Toxicology Studies" Toxicological Sciences 117(2):485-492.

Thomson Reuters Drug New, "Coadministration of long-acting GSK-744 and rilpivirine found feasible" [downloaded on the web http://drugnews.thomson-pharma.com/ddn/article.do?id=124544] Jul. 8, 2013 8:33:31 AM on Mon Jul. 8, 2013, 1 page; retrieved byHaolun Jin.
Thomson Reuters Drug News "Results from phase III trials of dolutegravir presented," Fri Jul. 5, 2013, 1 page; retrieved by Haolun Jin.
Trinite, B. et al. (2013) "An HIV-1 Replication Pathway Utilizing Reverse Transcription Products That Fail to Integrate" Journal of Virology 87(23):12701-12720.
Tseng, A. et al. (2014) "Drug Interactions with Integrase Inhibitors" Pharm. D.
Van Lunzen, J. et al. (2012) "Once daily dolutegravir (S/GSK1349572) in combination therapy in antiretroviral-naive adults with HIV: planned interim 48 week results from SPRING-1, a dose-ranging, randomised, phase 2b trial" Lancet Infectious Disease12(2):111-118.
Wai, J., et al. (2007) "Dihydroxypyridopyrazine-1,6-dione HIV-1 Integrase Inhibitors" Bioorganic & Medicinal Chemistry Letters; 17:5595-5599.
Walmsley, S. et al. (2012) "Dolutegravir (DTG; S/GSK1349572) + Abacavir/Lamivudine Once Daily Statistically Superior to Tenofovir/Emtricitabine/Efavirenz: 48-Week Results—SINGLE (ING114467)" Presentation H-556b; 52nd Interscience Conference onAntimicrobial Agents and Chemotherapy; Sep. 9-12; San Francisco, CA.
Walmsley, S. et al. (2013) "Dolutegravir plus Abacavir-Lamivudine for the Treatment of HIV-1 Infection" N Engl J Med 369(19):1807-1818.
Wang, F. et al. (1999) "Modifications of norditerpenoid alkaloids. I. N-deethylation reactions" Abstract, Chinese Chemical Letters 10(5):375-378.
Wang, F. et al. (2005) "To seek an approach toward the chemical conversion of C19-diterpenoid alkaloids to taxoids" Tetrahedron 61(8):2149-2167.
Wang, H. et al. (2015) "An Efficient and Highly Diastereoselective Synthesis of GSK1265744, a Potent HIV Integrase Inhibitor" Org. Letters 17:564-567.
Wang, Ying-Chuan, et al., "Switch in asymmetric induction sense in cycloadditions using camphor-based nitroso dienop," Tetrahedron: Asymmetry 13 (2002) 691-695.
Weller, S. et al. (2013) "Pharmacokinetics (PK) and Safety of Dolutegravir (DTG) in Subjects With Severe Renal Impairment and Healthy Controls" Poster A-1571; 53rd Interscience Conference on Antimicrobial Agents and Chemotherapy; Sep. 10-13; Denver, CO.
Weller, S., et al., "Bioequivalence of a Dolutegravir, Abacavir, and Lamivudine Fixed-Dose Combination Tablet and the Effect of Food," 53rd Interscience Conference on Antimicrobial Agents and Chemotherapy; Sep. 10-13, 2013, Denver, CO, 1 page.
Wensing, A. et al. (2014) "Special Contribution 2014 Update of the Drug Resistance Mutations in HIV-1" IAS-USA Topics in Antiviral Medicine 22(3):642-650.
Wolkowicz, U. et al. (2014) "Structural Basis of Mos1 Transposase Inhibition by the Anti-retroviral Drug Raltegravir" ACS Chem. Biol. 9:743-751.
Wu, B. et al. (2009) "Enantioselective Desymmetrization of meso-Aziridines with TMSN.sub.3 or TMSCN Catalyzed by Discrete Yttrium Complexes" Supporting Material Angew. Chem. Int. Ed. 48:1126-1129.
Zhang, X. et al. (2008) "Rapid analysis of a Chinese herbal prescription by liquid chromatography-time-of-flight tandem mass spectrometry" Abstract, Journal of Chromatography A 1206(2:140-146).
Zhao, X. et al. (2014) "4-Amino-1-hydroxy-2-oxo-1,8-naphthyridine-Containing Compounds Having High Potency against Raltegravir-Resistant Integrase Mutants of HIV-1" J Med Chem 57:5190-5202.
U.S. Appl. No. 14/815,504, filed Jul. 31, 2015, Haolun Jin et al.
International Preliminary Report on Patentability dated Dec. 29, 2016 for PCT/US2015/036757.

SODIUM (2R,5S,13AR)-7,9-DIOXO-10-((2,4,6-TRIFLUOROBENZYL)CARBAMOYL)-2,3,4,5,7, 9,13,13A-OCTAHYDRO-2,5-METHANOPYRIDO[ 1',2':4,5]PYRAZINO[2, 1-B][1, 3]OXAZEPIN-8-OLATE

CROSS REFERENCE TO RELATED APPLICATIONS

This application claims priority to and the benefit under 35 U.S.C. 119(e) of U.S. Provisional Patent Application Ser. No. 62/015,245, filed Jun. 20, 2014, the disclosure of which is hereby incorporated by reference in its entirety.

FIELD

The present invention relates to sodium (2R,5S,13aR)-7, 9-dioxo-10-((2,4,6-trifluorobenzyl)carbamoyl)-2,3,4,5,7,9, 13,13a-octahydro-2,5-methanopyrido[1',2':4,5]pyrazino[2, 1-b][1,3]oxazepin-8-olate, the crystalline forms, the pharmaceutical formulations, and the therapeutic uses thereof.

BACKGROUND

Human immunodeficiency virus infection and related diseases are a major public health problem worldwide. Human immunodeficiency virus type 1 (HIV-1) encodes three enzymes which are required for viral replication: reverse transcriptase, protease, and integrase. Although drugs targeting reverse transcriptase and protease are in wide use and have shown effectiveness, particularly when employed in combination, toxicity and development of resistant strains have limited their usefulness (Palella, et al. *N. Engl. J Med.* (1998) 338:853-860; Richman, D. D. *Nature* (2001) 410:995-1001).

A goal of antiretroviral therapy is to achieve viral suppression in the HIV infected patient. Treatment guidelines published by the United States Department of Health and Human Services provide that achievement of viral suppression requires the use of combination therapies, i.e., several drugs from at least two or more drug classes. In addition, decisions regarding the treatment of HIV infected patients are complicated when the patient requires treatment for other medical conditions. Because the standard of care requires the use of multiple different drugs to suppress HIV, as well as to treat other conditions the patient may be experiencing, the potential for drug interaction is a criterion for selection of a drug regimen. As such, there is a need for antiretroviral therapies having a decreased potential for drug interactions.

As discussed in co-pending application U.S. Ser. No. 14/133,855, filed Dec. 19, 2013 entitled "POLYCYCLIC-CARBAMOYLPYRIDONE COMPOUNDS AND THEIR PHARMACEUTICAL USE", (2R,5S,13aR)-8-hydroxy-7, 9-dioxo-N-(2,4,6-trifluorobenzyl)-2,3,4,5,7,9,13,13a-octahydro-2,5-methanopyrido[1',2':4,5]pyrazino[2,1-b][1,3]oxazepine-10-carboxamide demonstrates anti-viral activity. As discussed in co-pending application PCT Serial No. US2013/076367, filed Dec. 19, 2013 entitled "POLYCYCLIC-CARBAMOYLPYRIDONE COMPOUNDS AND THEIR PHARMACEUTICAL USE", (2R,5S,13aR)-8-hydroxy-7,9-dioxo-N-(2,4,6-trifluorobenzyl)-2,3,4,5,7,9,13, 13a-octahydro-2,5-methanopyrido[1',2':4,5]pyrazino[2,1-b] [1,3]oxazepine-10-carboxamide demonstrates anti-viral activity.

(2R,5S,13aR)-8-hydroxy-7,9-dioxo-N-(2,4,6-trifluorobenzyl)-2,3,4,5,7,9,13,13a-octahydro-2,5-methanopyrido [1',2':4,5]pyrazino[2,1-b][1,3]oxazepine-10-carboxamide, (Formula I), has the following structure:

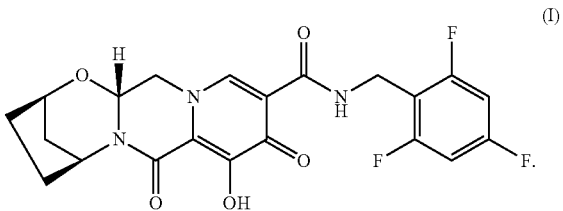 [SMILES: O=C(NCc1c(F)cc(F)cc1F)c1cn2c(c(O)c1=O)C(=O)N1[C@H]3CC[C@H](C3)O[C@@H]1C2]

It is desired to have physically stable forms of the compound that are suitable for the therapeutic use and the manufacturing process.

BRIEF SUMMARY

In certain embodiments, the present invention is directed to sodium (2R,5S,13aR)-7,9-dioxo-10-((2,4,6-trifluorobenzyl)carbamoyl)-2,3,4,5,7,9,13,13a-octahydro-2,5-methanopyrido[1',2':4,5]pyrazino[2,1-b][1,3]oxazepin-8-olate, having the following structure (Formula II):

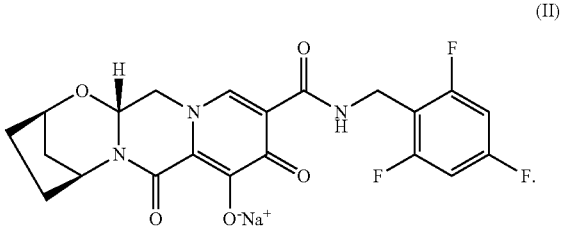

In a still further embodiment, the present invention is directed to crystalline sodium (2R,5S,13 aR)-7,9-dioxo-10-((2,4,6-trifluorobenzyl)carbamoyl)-2,3,4,5,7,9,13,13a-octahydro-2,5-methanopyrido[1',2':4,5]pyrazino[2,1-b][1,3]oxazepin-8-olate.

In a still further embodiment, the present invention is directed to sodium (2R,5S,13 aR)-7,9-dioxo-10-((2,4,6-trifluorobenzyl)carbamoyl)-2,3,4,5,7,9,13,13a-octahydro-2,5-methanopyrido[1',2':4,5]pyrazino[2,1-b][1,3]oxazepin-8-olate Form I.

In a certain embodiment, the present invention is directed to pharmaceutical formulations comprising sodium (2R,5S, 13aR)-7,9-dioxo-10-((2,4,6-trifluorobenzyl)carbamoyl)-2, 3,4,5,7,9,13,13a-octahydro-2,5-methanopyrido[1',2':4,5] pyrazino[2,1-b][1,3]oxazepin-8-olate.

In another embodiment, the present invention is directed to methods of treating or prophylactically preventing an HIV infection by administering sodium (2R,5S,13aR)-7,9-dioxo-10-((2,4,6-trifluorobenzyl)carbamoyl)-2,3,4,5,7,9,13,13a-octahydro-2,5-methanopyrido[1',2':4,5]pyrazino[2,1-b][1,3] oxazepin-8-olate.

In another embodiment, the present invention is directed to sodium (2R,5S,13aR)-7,9-dioxo-10-((2,4,6-trifluorobenzyl)carbamoyl)-2,3,4,5,7,9,13,13a-octahydro-2,5-methanopyrido[1',2':4,5]pyrazino[2,1-b][1,3]oxazepin-8-olate for use in methods of treating or prophylactically preventing an HIV infection.

In another embodiment, the present invention is directed to the use of sodium (2R,5S,13aR)-7,9-dioxo-10-((2,4,6-trifluorobenzyl)carbamoyl)-2,3,4,5,7,9,13,13a-octahydro-2,5-methanopyrido[1',2':4,5]pyrazino[2,1-b][1,3]oxazepin-8-olate in the manufacture of a medicament for treating or prophylactically preventing an HIV infection.

DETAILED DESCRIPTION

Figure 1:
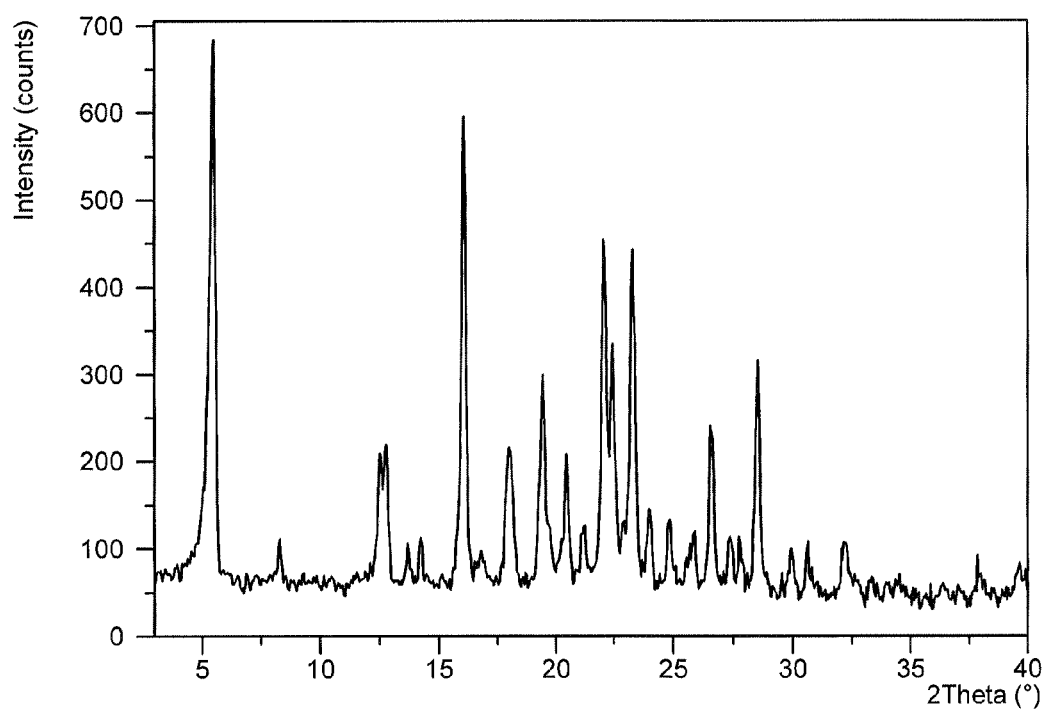
FIG. 1: XRPD pattern for sodium (2R,5S,13aR)-7,9-dioxo-10-((2,4,6-trifluorobenzyl)carbamoyl)-2,3,4,5,7,9,13,13a-octahydro-2,5-methanopyrido[1',2':4,5]pyrazino[2,1-b][1,3]oxazepin-8-olate Form I.

In the following description, certain specific details are set forth in order to provide a thorough understanding of various embodiments of the invention. However, one skilled in the art will understand that the invention may be practiced without these details. The description below of several embodiments is made with the understanding that the present disclosure is to be considered as an exemplification of the claimed subject matter, and is not intended to limit the appended claims to the specific embodiments illustrated. The headings used throughout this disclosure are provided for convenience only and are not to be construed to limit the claims in any way. Embodiments illustrated under any heading may be combined with embodiments illustrated under any other heading.

DEFINITIONS

Unless the context requires otherwise, throughout the present specification and claims, the word "comprise" and variations thereof, such as, "comprises" and "comprising" are to be construed in an open, inclusive sense, that is as "including, but not limited to".

Reference throughout this specification to "one embodiment" or "an embodiment" means that a particular feature, structure or characteristic described in connection with the embodiment is included in at least one embodiment of the present invention. Thus, the appearances of the phrases "in one embodiment" or "in an embodiment" in various places throughout this specification are not necessarily all referring to the same embodiment. Furthermore, the particular features, structures, or characteristics may be combined in any suitable manner in one or more embodiments.

The invention disclosed herein is also meant to encompass all pharmaceutically acceptable compounds of Formulas (I) and (II) being isotopically-labeled by having one or more atoms replaced by an atom having a different atomic mass or mass number. Examples of isotopes that can be incorporated into the disclosed compounds include isotopes of hydrogen, carbon, nitrogen, oxygen, phosphorous, fluorine, chlorine, and iodine, such as $^{2}H$, $^{3}H$, $^{11}C$, $^{13}C$, $^{14}C$, $^{13}N$, $^{15}N$, $^{15}O$, $^{18}O$, $^{31}P$, $^{32}P$, $^{35}S$, $^{18}F$, $^{36}Cl$, $^{123}I$, and $^{125}I$, respectively. These radiolabeled compounds could be useful to help determine or measure the effectiveness of the compounds, by characterizing, for example, the site or mode of action, or binding affinity to pharmacologically important site of action. Certain isotopically-labeled compounds of Formulas (I) and (II), for example, those incorporating a radioactive isotope, are useful in drug and/or substrate tissue distribution studies. The radioactive isotopes tritium, i.e. $^{3}H$, and carbon-14, i.e. $^{14}C$, are particularly useful for this purpose in view of their ease of incorporation and ready means of detection.

Substitution with heavier isotopes such as deuterium, i.e. $^{2}H$, may afford certain therapeutic advantages resulting from greater metabolic stability. For example, in vivo half-life may increase or dosage requirements may be reduced. Thus, heavier isotopes may be preferred in some circumstances.

Substitution with positron emitting isotopes, such as $^{11}C$, $^{18}F$, $^{15}O$, and $^{13}N$, can be useful in Positron Emission Topography (PET) studies for examining substrate receptor occupancy. Isotopically-labeled compounds of Formulas (I) and (II) can generally be prepared by conventional techniques known to those skilled in the art or by processes analogous to those described in the Examples as set out below using an appropriate isotopically-labeled reagent in place of the non-labeled reagent previously employed.

"Stable compound" and "stable structure" are meant to indicate a compound that is sufficiently robust to survive isolation to a useful degree of purity from a reaction mixture, and formulation into an efficacious therapeutic agent.

"Optional" or "optionally" means that the subsequently described event or circumstances may or may not occur, and that the description includes instances where said event or circumstance occurs and instances in which it does not. For example, "optionally substituted aryl" means that the aryl radical may or may not be substituted and that the description includes both substituted aryl radicals and aryl radicals having no substitution.

"Pharmaceutically acceptable carrier, diluent or excipient" includes without limitation any adjuvant, carrier, excipient, glidant, sweetening agent, diluent, preservative, dye/colorant, flavor enhancer, surfactant, wetting agent, dispersing agent, suspending agent, stabilizer, isotonic agent, solvent, or emulsifier which has been approved by the United States Food and Drug Administration as being acceptable for use in humans or domestic animals.

A "pharmaceutical composition" refers to a formulation of a compound of the invention and a medium generally accepted in the art for the delivery of the biologically active compound to mammals, e.g., humans. Such a medium includes all pharmaceutically acceptable carriers, diluents or excipients therefor.

"Effective amount" or "therapeutically effective amount" refers to an amount of a compound according to the invention, which when administered to a patient in need thereof, is sufficient to effect treatment for disease-states, conditions, or disorders for which the compounds have utility. Such an amount would be sufficient to elicit the biological or medical response of a tissue system, or patient that is sought by a researcher or clinician. The amount of a compound according to the invention which constitutes a therapeutically effective amount will vary depending on such factors as the compound and its biological activity, the composition used for administration, the time of administration, the route of administration, the rate of excretion of the compound, the duration of the treatment, the type of disease-state or disorder being treated and its severity, drugs used in combination with or coincidentally with the compounds of the invention, and the age, body weight, general health, sex and diet of the patient. Such a therapeutically effective amount can be determined routinely by one of ordinary skill in the art having regard to their own knowledge, the state of the art, and this disclosure.

The term "treatment" as used herein is intended to mean the administration of a compound or composition according to the present invention to alleviate or eliminate symptoms of HIV infection and/or to reduce viral load in a patient. The term "treatment" also encompasses the administration of a compound or composition according to the present invention post-exposure of the individual to the virus but before the appearance of symptoms of the disease, and/or prior to the detection of the virus in the blood, to prevent the appearance of symptoms of the disease and/or to prevent the virus from reaching detectible levels in the blood, and the administration of a compound or composition according to the present invention to prevent perinatal transmission of HIV from mother to baby, by administration to the mother before giving birth and to the child within the first days of life. In certain embodiments, the term "treatment" as used herein is intended to mean the administration of a compound or composition according to the present invention to alleviate or eliminate symptoms of HIV infection and/or to reduce viral load in a patient. In certain embodiments, the term "treatment" as used herein is further or alternatively intended to mean the administration of a compound or composition according to the present invention to maintain a reduced viral load in a patient. The term "treatment" also encompasses the administration of a compound or composition according to the present invention post-exposure of the individual to the virus but before the appearance of symptoms of the disease; and/or prior to the detection of the virus in the blood, to prevent the appearance of symptoms of the disease and/or to prevent the virus from reaching detectible levels in the blood, and the administration of a compound or composition according to the present invention to prevent perinatal transmission of HIV from mother to baby, by administration to the mother before giving birth and to the child within the first days of life. In certain embodiments, the term "treatment" as used herein is further or alternatively intended to mean the administration of a compound or composition according to the present invention post-exposure of the individual to the virus as a subsequent or additional therapy to a first-line therapy (e.g., for maintenance of low viral load).

"Prevention" or "preventing" means any treatment of a disease or condition that causes the clinical symptoms of the disease or condition not to develop. The term "prevention" also encompasses the administration of a compound or composition according to the present invention pre-exposure of the individual to the virus (e.g., pre-exposure prophylaxis), to prevent the appearance of symptoms of the disease and/or to prevent the virus from reaching detectible levels in the blood.

The terms "Subject" or "patient" refer to an animal, such as a mammal (including a human), that has been or will be the object of treatment, observation or experiment. The methods described herein may be useful in human therapy and/or veterinary applications. In some embodiments, the subject is a mammal (or the patient). In some embodiments the subject (or the patient) is human, domestic animals (e.g., dogs and cats), farm animals (e.g., cattle, horses, sheep, goats and pigs), and/or laboratory animals (e.g., mice, rats, hamsters, guinea pigs, pigs, rabbits, dogs, and monkeys). In one embodiment, the subject (or the patient) is a human. "Human (or patient) in need thereof" refers to a human who may have or is suspect to have diseases or conditions that would benefit from certain treatment; for example, being treated with the compounds disclosed herein according to the present application.

The term "antiviral agent" as used herein is intended to mean an agent (compound or biological) that is effective to inhibit the formation and/or replication of a virus in a human being, including but not limited to agents that interfere with either host or viral mechanisms necessary for the formation and/or replication of a virus in a human being.

The term "inhibitor of HIV replication" as used herein is intended to mean an agent capable of reducing or eliminating the ability of HIV to replicate in a host cell, whether in vitro, ex vivo or in vivo.

A "tautomer" refers to a proton shift from one atom of a molecule to another atom of the same molecule. The present invention includes tautomers of any said compounds.

Reference to "about" a value or parameter herein includes (and describes) embodiments that are directed to that value or parameter per se. For example, description referring to "about X" includes description of "X". Also, the singular forms "a" and "the" include plural references unless the context clearly dictates otherwise. Thus, e.g., reference to "the compound" includes a plurality of such compounds and reference to "the assay" includes reference to one or more assays and equivalents thereof known to those skilled in the art.

"Pharmaceutically acceptable" or "physiologically acceptable" refer to compounds, salts, compositions, dosage forms and other materials which are useful in preparing a pharmaceutical composition that is suitable for veterinary or human pharmaceutical use.

"Unit dosage forms" are physically discrete units suitable as unitary dosages for subjects (e.g., human subjects and other mammals), each unit containing a predetermined quantity of active material calculated to produce the desired therapeutic effect, in association with a suitable pharmaceutical carrier.

Crystalline Form

Formula II

It is desirable to develop a crystalline form of sodium (2R,5S,13aR)-7,9-dioxo-10-((2,4,6-trifluorobenzyl)carbamoyl)-2,3,4,5,7,9,13,13a-octahydro-2,5-methanopyrido[1',2':4,5]pyrazino[2,1-b][1,3]oxazepin-8-olate that may be useful in the synthesis of sodium (2R,5S,13aR)-7,9-dioxo-10-((2,4,6-trifluorobenzyl)carbamoyl)-2,3,4,5,7,9,13,13a-octahydro-2,5-methanopyrido[1',2':4,5]pyrazino[2,1-b][1,3]oxazepin-8-olate. A form of sodium (2R,5S,13aR)-7,9-dioxo-10-((2,4,6-trifluorobenzyl)carbamoyl)-2,3,4,5,7,9,13,13a-octahydro-2,5-methanopyrido[1',2':4,5]pyrazino[2,1-b][1,3]oxazepin-8-olate may be an intermediate to the synthesis of sodium (2R,5S,13aR)-7,9-dioxo-10-((2,4,6-trifluorobenzyl) carbamoyl)-2,3,4,5,7,9,13,13a-octahydro-2,5-methanopyrido[1',2':4,5]pyrazino[2,1-b][1,3]oxazepin-8-olate. A form of sodium (2R,5S,13aR)-7,9-dioxo-10-((2,4,6-trifluorobenzyl)carbamoyl)-2,3,4,5,7,9,13,13a-octahydro-2,5-methanopyrido[1',2':4,5]pyrazino[2,1-b][1,3]oxazepin-8-olate may be the final product in the synthesis of sodium (2R,5S,13aR)-7,9-dioxo-10-((2,4,6-trifluorobenzyl)carbamoyl)-2,3,4,5,7,9,13,13a-octahydro-2,5-methanopyrido[1',2':4,5]pyrazino[2,1-b][1,3]oxazepin-8-olate. A polymorphic form or polymorph or cocrystal may have properties such as bioavailability and stability at certain conditions that may be suitable for medical or pharmaceutical uses.

A crystalline form of sodium (2R,5S,13aR)-7,9-dioxo-10-((2,4,6-trifluorobenzyl)carbamoyl)-2,3,4,5,7,9,13,13a-octahydro-2,5-methanopyrido[1',2':4,5]pyrazino[2,1-b][1,3]oxazepin-8-olate may provide the advantage of bioavailability and stability, suitable for use as an active ingredient in a pharmaceutical composition. In certain embodiments, a crystalline form sodium (2R,5S,13aR)-7,9-dioxo-10-((2,4,6-trifluorobenzyl)carbamoyl)-2,3,4,5,7,9,13,13a-octahydro-2,5-methanopyrido[1',2':4,5]pyrazino[2,1-b][1,3]oxazepin-8-olate provides an advantage of improved bioavailability (Table 3) and/or stability (Table 4). Variations in the crystal structure of a pharmaceutical drug substance or active ingredient may affect the dissolution rate (which may affect bioavailability, etc.), manufacturability (e.g., ease of handling, ability to consistently prepare doses of known strength) and stability (e.g., thermal stability, shelf life, etc.) of a pharmaceutical drug product or active ingredient. Such variations may affect the preparation or formulation of pharmaceutical compositions in different dosage or delivery forms, such as solid oral dosage form including tablets and capsules. Compared to other forms such as non-crystalline or amorphous forms, crystalline forms may provide desired or suitable hygroscopicity, particle size controls, dissolution rate, solubility, purity, physical and chemical stability, manufacturability, yield, and/or process control. Thus, crystalline forms of sodium (2R,5S,13aR)-7,9-dioxo-10-((2,4,6-trifluorobenzyl)carbamoyl)-2,3,4,5,7,9,13,13a-octahydro-2,5-methanopyrido[1',2':4,5]pyrazino[2,1-b][1,3]oxazepin-8-olate may provide advantages such as: improving the manufacturing process of an active agent or the stability or storability of a drug product form of the compound or an active ingredient, and/or having suitable bioavailability and/or stability as an active agent.

The use of certain solvents has been found to produce different polymorphic forms of sodium (2R,5S,13aR)-7,9-dioxo-10-((2,4,6-trifluorobenzyl)carbamoyl)-2,3,4,5,7,9,13,13a-octahydro-2,5-methanopyrido[1',2':4,5]pyrazino[2,1-b][1,3]oxazepin-8-olate, including polymorphic Form I, which may exhibit one or more favorable characteristics described above. In certain embodiments, Form I of sodium (2R,5S,13aR)-7,9-dioxo-10-((2,4,6-trifluorobenzyl)carbamoyl)-2,3,4,5,7,9,13,13a-octahydro-2,5-methanopyrido[1',2':4,5]pyrazino[2,1-b][1,3]oxazepin-8-olate provides an advantage of improved bioavailability (Table 3) and/or stability (Table 4). The processes for the preparation of the polymorphs described herein and characterization of these polymorphs are described in greater detail below.

The compound name provided above is named using ChemBioDraw Ultra and one skilled in the art understands that the compound structure may be named or identified using other commonly recognized nomenclature systems and symbols. By way of example, the compound may be named or identified with common names, systematic or non-systematic names. The nomenclature systems and symbols that are commonly recognized in the art of chemistry including but not limited to Chemical Abstract Service (CAS) and International Union of Pure and Applied Chemistry (IUPAC). Accordingly, the compound structure provided above may be named or identified as sodium (2R,5S,13aR)-7,9-dioxo-10-((2,4,6-trifluorobenzyl)carbamoyl)-2,3,4,5,7,9,13,13a-octahydro-2,5-methanopyrido[1',2':4,5]pyrazino[2,1-b][1,3]oxazepin-8-olate under IUPAC.

In particular embodiments, crystalline forms of sodium (2R,5S,13aR)-7,9-dioxo-10-((2,4,6-trifluorobenzyl)carbamoyl)-2,3,4,5,7,9,13,13a-octahydro-2,5-methanopyrido[1',2':4,5]pyrazino[2,1-b][1,3]oxazepin-8-olate are disclosed.

Formula II, Form I

In a certain embodiment, novel forms of sodium (2R,5S,13aR)-7,9-dioxo-10-((2,4,6-trifluorobenzyl)carbamoyl)-2,3,4,5,7,9,13,13a-octahydro-2,5-methanopyrido[1',2':4,5]pyrazino[2,1-b][1,3]oxazepin-8-olate, having the following structure (Formula II) are disclosed:

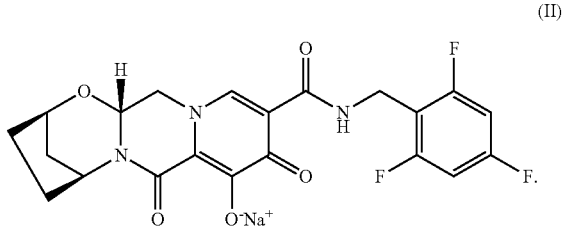

(II)

In a further embodiment, crystalline forms of sodium (2R,5S,13aR)-7,9-dioxo-10-((2,4,6-trifluorobenzyl)carbamoyl)-2,3,4,5,7,9,13,13a-octahydro-2,5-methanopyrido[1',2':4,5]pyrazino[2,1-b][1,3]oxazepin-8-olate are disclosed.

In a certain embodiment, sodium (2R,5S,13aR)-7,9-dioxo-10-((2,4,6-trifluorobenzyl)carbamoyl)-2,3,4,5,7,9,13,13a-octahydro-2,5-methanopyrido[1',2':4,5]pyrazino[2,1-b][1,3]oxazepin-8-olate Form I is disclosed.

Figure 2:
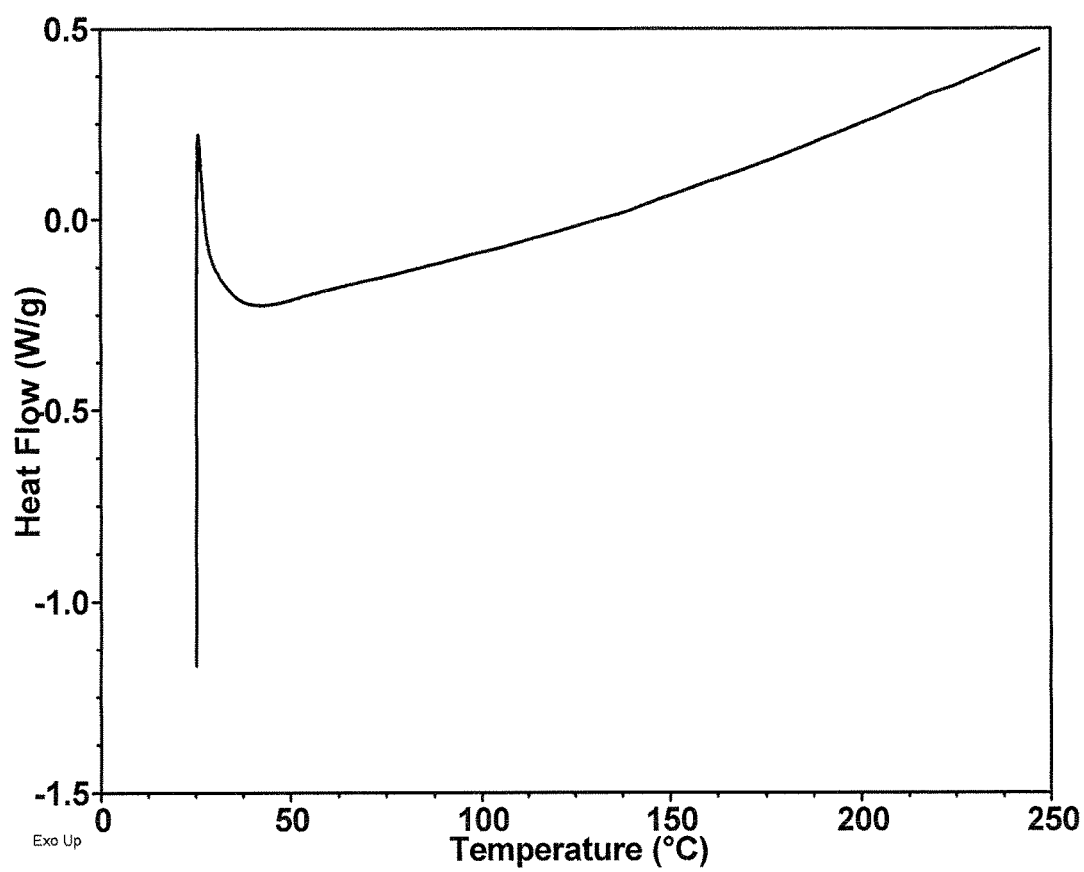
FIG. 2: DSC for sodium (2R,5S,13aR)-7,9-dioxo-10-((2,4,6-trifluorobenzyl)carbamoyl)-2,3,4,5,7,9,13,13a-octahydro-2,5-methanopyrido[1',2':4,5]pyrazino[2,1-b][1,3]oxazepin-8-olate Form I.
Figure 3:
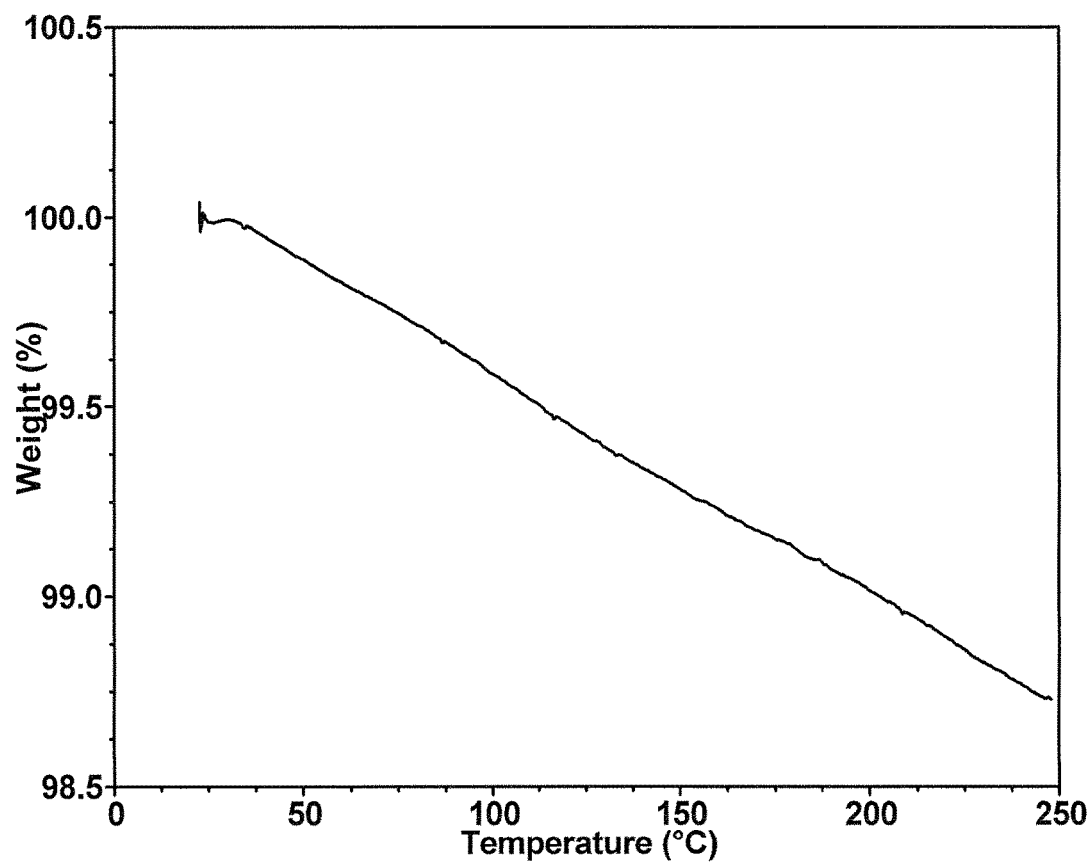
FIG. 3: TGA for sodium (2R,5S,13aR)-7,9-dioxo-10-((2,4,6-trifluorobenzyl)carbamoyl)-2,3,4,5,7,9,13,13a-octahydro-2,5-methanopyrido[1',2':4,5]pyrazino[2,1-b][1,3]oxazepin-8-olate Form I.
Figure 4:
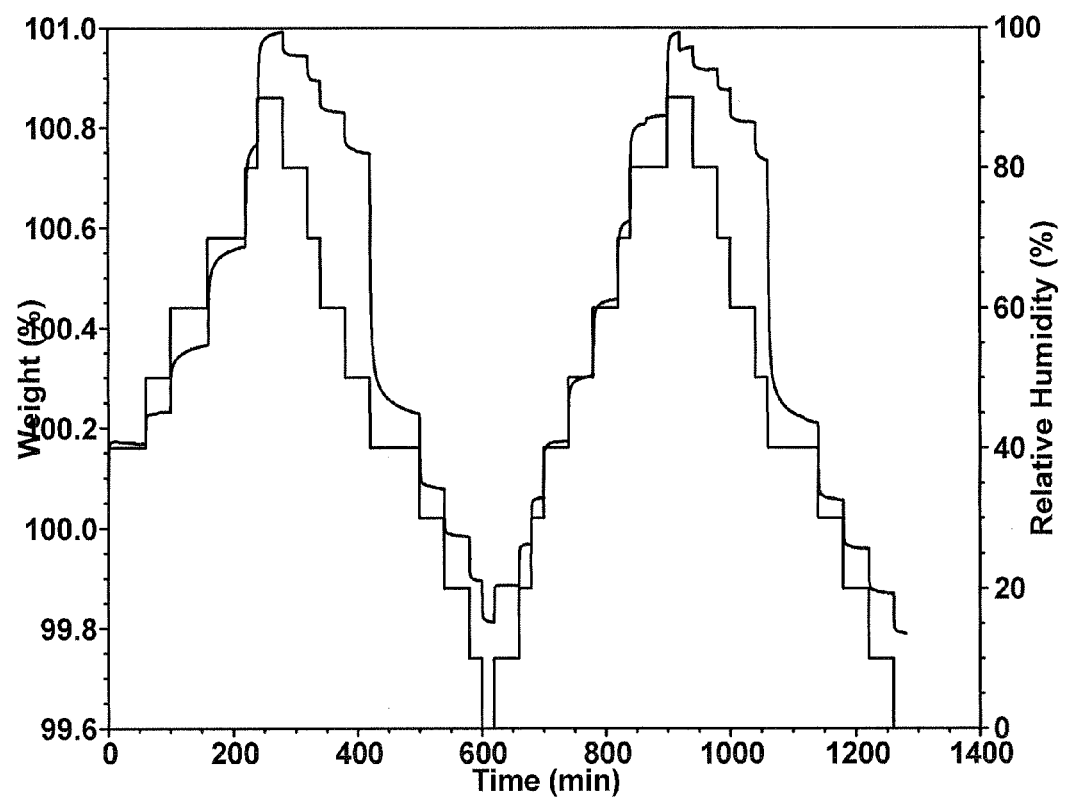
FIG. 4: DVS for sodium (2R,5S,13aR)-7,9-dioxo-10-((2,4,6-trifluorobenzyl)carbamoyl)-2,3,4,5,7,9,13,13a-octahydro-2,5-methanopyrido[1',2':4,5]pyrazino[2,1-b][1,3]oxazepin-8-olate Form I.
Figure 8:
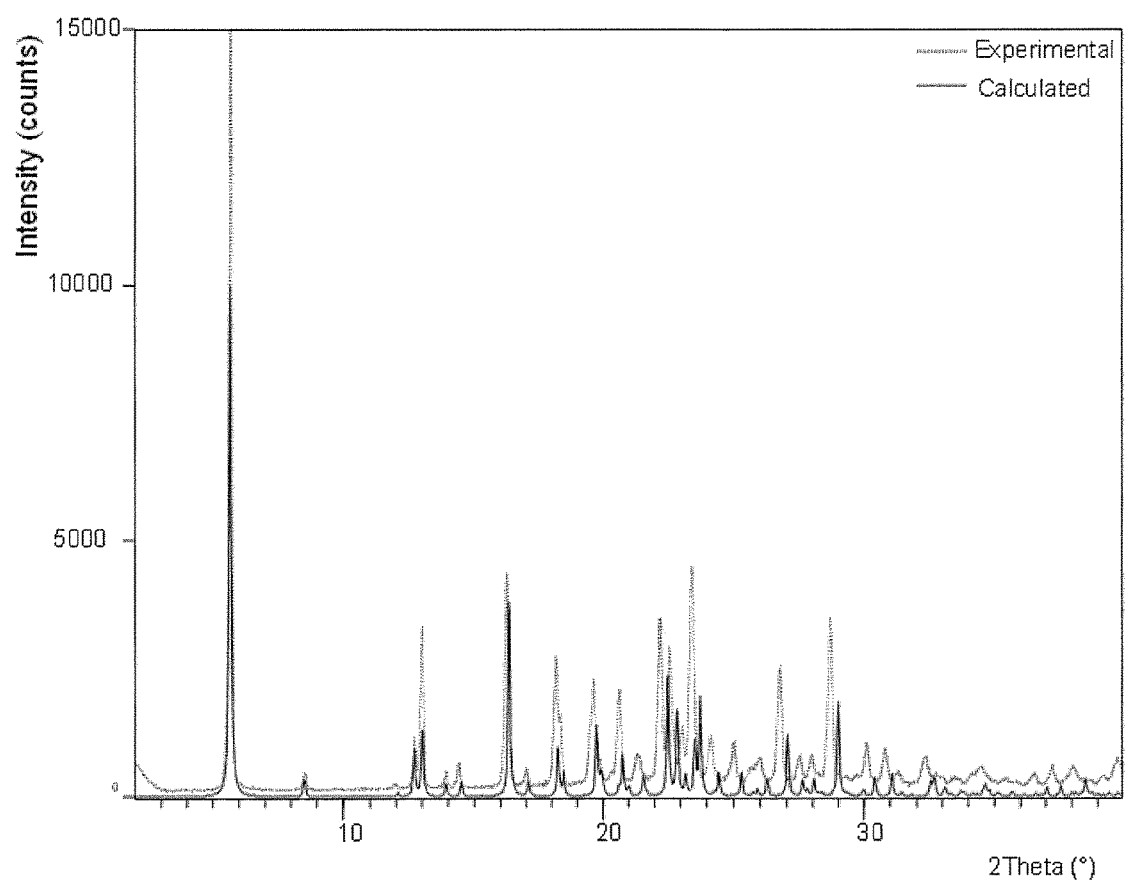
FIG. 8: Calculated and Experimental XRPD pattern for sodium (2R,5S,13aR)-7,9-dioxo-10-((2,4,6-trifluorobenzyl)carbamoyl)-2,3,4,5,7,9,13,13a-octahydro-2,5-methanopyrido[1',2':4,5]pyrazino[2,1-b][1,3]oxazepin-8-olate Form I.

In one embodiment, provided is polymorphic Form I of sodium (2R,5S,13aR)-7,9-dioxo-10-((2,4,6-trifluorobenzyl)carbamoyl)-2,3,4,5,7,9,13,13a-octahydro-2,5-methanopyrido[1',2':4,5]pyrazino[2,1-b][1,3]oxazepin-8-olate, wherein the polymorph exhibits an X-ray powder diffraction (XRPD) pattern substantially as shown in FIG. 1 and/or FIG. 8. Polymorphic sodium Form I may exhibit a differential scanning calorimetry (DSC) thermogram substantially as shown in FIG. 2. Polymorphic sodium Form I may exhibit a thermographic analysis (TGA) graph substantially as shown in FIG. 3. Polymorphic sodium Form I may exhibit dynamic vapour sorption (DVS) graphs substantially as shown in FIG. 4.

The term "substantially as shown in" when referring, for example, to an XRPD pattern, a DSC thermogram, or a TGA graph includes a pattern, thermogram or graph that is not necessarily identical to those depicted herein, but that falls within the limits of experimental error or deviations when considered by one of ordinary skill in the art.

Polymorphic sodium Form I may have a unit cell as determined by crystal X-ray crystallography of the following dimensions: a=8.9561 (10) Å; b=13.9202 (14) Å; c=31.115 (3) Å; α=90°; β=90°; and γ=90°.

In some embodiments of polymorphic sodium Form I, at least one, at least two, at least three, at least four, at least five, at least six, at least seven, at least eight, at least nine, or all of the following (a)-(j) apply: (a) polymorphic Form I has an XRPD pattern substantially as shown in FIG. 1 and/or FIG.

8; (b) polymorphic sodium Form I has a DSC thermogram substantially as shown in FIG. 2; (c) polymorphic sodium Form I has a TGA graph substantially as shown in FIG. 3; (d) polymorphic sodium Form I has DVS graphs substantially as shown in FIG. 4; (e) polymorphic sodium Form I has a unit cell, as determined by crystal X-ray crystallography, of the following dimensions: a=8.9561 (10) Å; b=13.9202 (14) Å; c=31.115 (3) Å; α=90°; β=90°; and γ=90°; (f) polymorphic sodium Form I has an orthorhombic crystal system; (g) polymorphic sodium Form I has a P212121 space group; (h) polymorphic sodium Form I has a volume of 3879.2 (7) Å$^3$; (i) polymorphic Form I has a Z value of 4; and (j) polymorphic Form I has a density of 1.614 Mg/m$^3$.

In some embodiments, polymorphic sodium Form I has at least one, at least two, at least three, at least four, or all of the following properties:

a. an XRPD pattern substantially as shown in FIG. 1 and/or FIG. 8;
b. a DSC thermogram substantially as shown in FIG. 2;
c. TGA graphs substantially as shown in FIG. 3;
d. DVS graphs substantially as shown in FIG. 4; and
e. a unit cell, as determined by crystal X-ray crystallography, of the following dimensions a=8.9561 (10) Å; b=13.9202 (14) Å; c=31.115 (3) Å; α=90°; β=90°; and γ=90°;

In some embodiments, polymorphic sodium Form I has an XRPD pattern displaying at least two, at least three, at least four, at least five, or at least six of the degree 2θ-reflections with the greatest intensity as the XRPD pattern substantially as shown in FIG. 1 and/or FIG. 8.

In certain embodiments, polymorphic sodium Form I has an XRPD pattern comprising degree 2θ-reflections (+/−0.2 degrees 2θ) at 5.5, 16.1, and 23.3. In one embodiment, polymorphic sodium Form I has an XRPD pattern comprising degree 2θ-reflections (+/−0.2 degrees 2θ) at 5.5, 16.1, and 23.3 and one or more of the degree 2θ-reflections (+/−0.2 degrees 2θ) at 22.1, 28.5, and 22.5. In one embodiment, polymorphic sodium Form I has an XRPD pattern comprising degree 2θ-reflections (+/−0.2 degrees 2θ) at 5.5, 16.1, and 23.3 and one of the degree 2θ-reflections (+/−0.2 degrees 2θ) at 22.1, 28.5, and 22.5. In one embodiment, polymorphic sodium Form I has an XRPD pattern comprising degree 2θ-reflections (+/−0.2 degrees 2θ) at 5.5, 16.1, and 23.3 and two of the degree 2θ-reflections (+/−0.2 degrees 2θ) at 22.1, 28.5, and 22.5. In one embodiment, polymorphic sodium Form I has an XRPD pattern comprising degree 2θ-reflections (+/−0.2 degrees 2θ) at 5.5, 16.1, and 23.3 and three of the degree 2θ-reflections (+/−0.2 degrees 2θ) at 22.1, 28.5, and 22.5. In one embodiment, polymorphic sodium Form I has an XRPD pattern comprising degree 2θ-reflections (+/−0.2 degrees 2θ) at 5.5, 16.1, 23.3, 22.1, 28.5, and 22.5. In one embodiment, polymorphic sodium Form I has an XRPD pattern comprising degree 2θ-reflections (+1-0.2 degrees 2θ) at 5.5, 16.1, 23.3, 22.1, 28.5, 22.5, 19.5, and 26.6. In one embodiment, polymorphic sodium Form I has an XRPD pattern comprising any three degree 2θ-reflections (+/−0.2 degrees 2θ) selected from the group consisting of 5.5, 16.1, 23.3, 22.1, 28.5, 22.5, 19.5, 26.6, and 17.9.

Pharmaceutical Compositions

For the purposes of administration, in certain embodiments, the compounds described herein are administered as a raw chemical or are formulated as pharmaceutical compositions. Pharmaceutical compositions of the present invention comprise a compound of Formula (II), including forms and co-crystals thereof, and a pharmaceutically acceptable carrier, diluent or excipient. The compound of Formula (II) is present in the composition in an amount which is effective to treat a particular disease or condition of interest. The activity of compounds of Formula (II) can be determined by one skilled in the art, for example, as described in co-pending application Ser. No. 14/133,855, filed Dec. 19, 2013 entitled "POLYCYCLIC-CARBAMOYLPYRIDONE COMPOUNDS AND THEIR PHARMACEUTICAL USE". The activity of compounds of Formula (II) can also be determined by one skilled on the art, for example, as described in co-pending PCT Serial No. US2013/076367, filed Dec. 19, 2013 entitled, "POLYCYCLIC-CARBAMOYLPYRIDONE COMPOUNDS AND THEIR PHARMACEUTICAL USE." Appropriate concentrations and dosages can be readily determined by one skilled in the art. In certain embodiments, a compound of Formula (II) is present in the pharmaceutical composition in an amount from about 25 mg to about 500 mg. In certain embodiments, a compound of Formula (II) is present in the pharmaceutical composition in an amount of about 100 mg to about 300 mg. In certain embodiments, a compound of Formula (II) is present in the pharmaceutical composition in an amount of about 5 mg to about 100 mg. In certain embodiments, a compound of Formula (II) is present in the pharmaceutical composition in an amount of about 25 mg to about 100 mg. In certain embodiments, a compound of Formula (II) is present in the pharmaceutical composition in an amount of about 50 mg to about 100 mg. In certain embodiments, a compound of Formula (II) is present in the pharmaceutical composition in an amount of about 5 mg to about 100 mg. In certain embodiments, a compound of Formula (II) is present in the pharmaceutical composition in an amount of about 5 mg, 25 mg, 50 mg, 75, mg, 100 mg, 200 mg, 300 mg, 400 mg or about 500 mg.

Formula II

Provided are also compositions comprising at least one polymorph (e.g., any one or more of Formula II polymorphic Forms I) as described herein. In a particular embodiment, a composition comprising Formula II polymorphic Form I, described herein is provided. In other embodiments, the compositions described herein may comprise substantially pure polymorphic forms, or may be substantially free of other polymorphs and/or impurities.

In some embodiments, the composition comprises a polymorphic form of sodium (2R,5S,13aR)-7,9-dioxo-10-((2,4,6-trifluorobenzyl)carbamoyl)-2,3,4,5,7,9,13,13a-octahydro-2,5-methanopyrido[1',2':4,5]pyrazino[2,1-b][1,3]oxazepin-8-olate. In certain embodiments are provided compositions comprising a polymorphic form as described herein, wherein the sodium (2R,5S,13aR)-7,9-dioxo-10-((2,4,6-trifluorobenzyl)carbamoyl)-2,3,4,5,7,9,13,13a-octahydro-2,5-methanopyrido[1',2':4,5]pyrazino[2,1-b][1,3]oxazepin-8-olate within the composition is substantially pure (i.e., substantially pure Form I). In particular embodiments of compositions comprising a polymorphic form of sodium (2R,5S,13aR)-7,9-dioxo-10-((2,4,6-trifluorobenzyl)carbamoyl)-2,3,4,5,7,9,13,13a-octahydro-2,5-methanopyrido[1',2': 4,5]pyrazino[2,1-b][1,3]oxazepin-8-olate, at least about 50%, at least about 60%, at least about 70%, at least about 80%, at least about 85%, at least about 90%, at least about 95%, at least about 96%, at least about 97%, at least about 98%, or at least about 99% of sodium (2R,5S,13aR)-7,9-dioxo-10-((2,4,6-trifluorobenzyl)carbamoyl)-2,3,4,5,7,9,13, 13a-octahydro-2,5-methanopyrido[1',2':4,5]pyrazino[2,1-b][1,3]oxazepin-8-olate present in the composition is Formula II, Form I, disclosed herein. In certain embodiments, the composition includes at least about 50%, at least about 60%, at least about 70%, at least about 80%, at least about 85%, at least about 90%, at least about 95%, at least about 96%, at least about 97%, at least about 98%, or at least about 99% of Form I of sodium (2R,5S,13aR)-7,9-dioxo-10-((2,4,6-trifluorobenzyl)carbamoyl)-2,3,4,5,7,9,13,13a-octahydro-2,5-methanopyrido[1',2':4,5]pyrazino[2,1-b][1,3]oxazepin-8-olate.

In other embodiments of compositions comprising a polymorphic form disclosed herein, less than about 50%, less than about 40%, less than about 30%, less than about 20%, less than about 10%, less than about 5%, less than about 4%, less than about 3%, less than about 2% or less than about 1% of sodium (2R,5S,13aR)-7,9-dioxo-10-((2,4,6-trifluorobenzyl)carbamoyl)-2,3,4,5,7,9,13,13a-octahydro-2,5-methanopyrido[1',2':4,5]pyrazino[2,1-b][1,3]oxazepin-8-olate present in the composition are other polymorphs of sodium (2R,5S,13aR)-7,9-dioxo-10-((2,4,6-trifluorobenzyl)carbamoyl)-2,3,4,5,7,9,13,13a-octahydro-2,5-methanopyrido[1',2':4,5]pyrazino[2,1-b][1,3]oxazepin-8-olate and/or impurities.

In yet other embodiments of compositions comprising the polymorphic forms disclosed herein, impurities make up less than about 5%, less than about 4%, less than about 3%, less than about 2% or less than about 1% of the total mass relative to the mass of the polymorphic forms present. Impurities may, for example, include by-products from synthesizing sodium (2R,5S,13aR)-7,9-dioxo-10-((2,4,6-trifluorobenzyl)carbamoyl)-2,3,4,5,7,9,13,13a-octahydro-2,5-methanopyrido[1',2':4,5]pyrazino[2,1-b][1,3]oxazepin-8-olate, contaminants, degradation products, other polymorphic forms, amorphous form, water, and solvents. In certain embodiments, impurities include by-products from the process of synthesizing sodium (2R,5S,13aR)-7,9-dioxo-10-((2,4,6-trifluorobenzyl)carbamoyl)-2,3,4,5,7,9,13,13a-octahydro-2,5-methanopyrido[1',2':4,5]pyrazino[2,1-b][1,3]oxazepin-8-olate. In certain embodiments, impurities include contaminants from the process of synthesizing sodium (2R,5S,13aR)-7,9-dioxo-10-((2,4,6-trifluorobenzyl)carbamoyl)-2,3,4,5,7,9,13,13a-octahydro-2,5-methanopyrido[1',2':4,5]pyrazino[2,1-b][1,3]oxazepin-8-olate. In certain embodiments, impurities include degradation products of sodium (2R,5S,13aR)-7,9-dioxo-10-((2,4,6-trifluorobenzyl)carbamoyl)-2,3,4,5,7,9,13,13a-octahydro-2,5-methanopyrido[1',2':4,5]pyrazino[2,1-b][1,3]oxazepin-8-olate. In certain embodiments, impurities include other polymorphic forms of sodium (2R,5S,13aR)-7,9-dioxo-10-((2,4,6-trifluorobenzyl)carbamoyl)-2,3,4,5,7,9,13,13a-octahydro-2,5-methanopyrido[1',2':4,5]pyrazino[2,1-b][1,3]oxazepin-8-olate. In certain embodiments, impurities include water or solvent. In certain embodiments of compositions comprising a polymorphic form disclosed herein, impurities are selected from the group consisting of by-products from synthesizing sodium (2R,5S,13aR)-7,9-dioxo-10-((2,4,6-trifluorobenzyl)carbamoyl)-2,3,4,5,7,9,13,13a-octahydro-2,5-methanopyrido[1',2':4,5]pyrazino[2,1-b][1,3]oxazepin-8-olate, contaminants, degradation products, other polymorphic forms, water, solvents and combinations thereof.

In yet other embodiments, the composition comprising Formula II, Form I disclosed herein has less than about 5%, less than about 4%, less than about 3%, less than about 2%, or less than about 1% by weight of amorphous or non-crystalline sodium (2R,5S,13aR)-7,9-dioxo-10-((2,4,6-trifluorobenzyl)carbamoyl)-2,3,4,5,7,9,13,13a-octahydro-2,5-methanopyrido[1',2':4,5]pyrazino[2,1-b][1,3]oxazepin-8-olate.

In some embodiments, the term "substantially pure" or "substantially free" with respect to a particular polymorphic form of a compound means that the composition comprising the polymorphic form contains less than 95%, less than 90%, less than 80%, less than 70%, less than 65%, less than 60%, less than 55%, less than 50%, less than 40%, less than 30%, less than 20%, less than 15%, less than 10%, less than 5%, or less than 1% by weight of other substances, including other polymorphic forms and/or impurities. In certain embodiments, "substantially pure" or "substantially free of" refers to a substance free of other substances, including other polymorphic forms and/or impurities. Impurities may, for example, include by-products or left over reagents from chemical reactions, contaminants, degradation products, other polymorphic forms, water, and solvents.

Administration

Administration of the compounds disclosed herein in pure form or in an appropriate pharmaceutical composition, can be carried out via any of the accepted modes of administration of agents for serving similar utilities. The pharmaceutical compositions described herein can be prepared by combining a compound disclosed herein with an appropriate pharmaceutically acceptable carrier, diluent or excipient, and may be formulated into preparations in solid, semi-solid, liquid or gaseous forms, such as tablets, capsules, powders, granules, ointments, solutions, suppositories, injections, inhalants, gels, microspheres, and aerosols. The pharmaceutical compositions of the invention can be prepared by combining a compound of the invention with an appropriate pharmaceutically acceptable carrier, diluent or excipient, and may be formulated into preparations in solid, semi-solid, liquid or gaseous forms, such as solid dispersions and solid solutions. Typical routes of administering such pharmaceutical compositions include, without limitation, oral, topical, transdermal, inhalation, parenteral, sublingual, buccal, rectal, vaginal, and intranasal. In one embodiment, the pharmaceutical compositions is prepared for oral administration. In a specific embodiment, the pharmaceutical compositions is a tablet. Pharmaceutical compositions of the invention are formulated so as to allow the active ingredients contained therein to be bioavailable upon administration of the composition to a patient. Compositions that will be administered to a subject or patient take the form of one or more dosage units, where for example, a tablet may be a single dosage unit, and a container of a compound of the invention in aerosol form may hold a plurality of dosage units. Actual methods of preparing such dosage forms are known, or will be apparent, to those skilled in this art; for example, see *Remington: The Science and Practice of Pharmacy*, 20th Edition (Philadelphia College of Pharmacy and Science, 2000). The composition to be administered will, in any event, contain a therapeutically effective amount of a compound of the invention for treatment of a disease or condition of interest in accordance with the teachings of this disclosure.

The pharmaceutical compositions disclosed herein may be prepared by methodology well known in the pharmaceutical art. For example, a pharmaceutical composition intended to be administered by injection can be prepared by combining a compound of the invention with sterile, distilled water so as to form a solution. A surfactant may be added to facilitate the formation of a homogeneous solution or suspension. Surfactants are compounds that non-covalently interact with the compound of the invention so as to facilitate dissolution or homogeneous suspension of the compound in the aqueous delivery system.

For example, a solid pharmaceutical composition intended for oral administration can be prepared by mixing a compound of the invention with at least one suitable pharmaceutical excipient to form a solid preformulation composition, which then may be readily subdivided into equally effective unit dosage forms such as tablets, pills and capsules. Accordingly, in one embodiment, a pharmaceutical composition is provided, which includes a compound of Formula (II) and a pharmaceutical excipient.

The compounds disclosed herein are administered in a therapeutically effective amount, which will vary depending upon a variety of factors including the activity of the specific compound employed; the metabolic stability and length of action of the compound; the age, body weight, general health, sex, and diet of the patient; the mode and time of administration; the rate of excretion; the drug combination; the severity of the particular disorder or condition; and the subject undergoing therapy. In some embodiments, the compounds of the invention can be administered alone or in combination with other antiviral agents once or twice daily for as long as the patient is infected, latently infected, or to prevent infection (e.g. for multiple years, months, weeks, or days).

Combination Therapy

In one embodiment, a method for treating or preventing an HIV infection in a human having or at risk of having the infection is provided, comprising administering to the human a therapeutically effective amount of a compound disclosed herein in combination with a therapeutically effective amount of one or more (e.g., one, two, three, one or two, or one to three) additional therapeutic agents. In one embodiment, a method for treating an HIV infection in a human having or at risk of having the infection is provided, comprising administering to the human a therapeutically effective amount of a compound disclosed herein in combination with a therapeutically effective amount of one or more (e.g., one, two, three, one or two, or one to three) additional therapeutic agents.

In one embodiment, a method for treating an HIV infection in a human having or at risk of having the infection is provided, comprising administering to the human a therapeutically effective amount of a compound or composition disclosed herein in combination with a therapeutically effective amount of one or more (e.g., one, two, three, one or two, or one to three) additional therapeutic agents.

In certain embodiments, the present invention provides a method for treating an HIV infection, comprising administering to a patient in need thereof a therapeutically effective amount of a compound or composition disclosed herein in combination with a therapeutically effective amount of one or more additional therapeutic agents which are suitable for treating an HIV infection.

One embodiment provides a compound disclosed herein in combination with one or more (e.g., one, two, three, one or two, or one to three) additional therapeutic agents for use in a method for treating or preventing an HIV infection in a human having or at risk of having the infection. One embodiment provides a compound disclosed herein in combination with one or more (e.g., one, two, three, one or two, or one to three) additional therapeutic agents for use in a method for treating an HIV infection in a human having or at risk of having the infection. One embodiment provides a compound disclosed herein for use in a method for treating or preventing an HIV infection in a human having or at risk of having the infection, wherein the compound is administered in combination with one or more (e.g., one, two, three, one or two, or one to three) additional therapeutic agents. One embodiment provides a compound disclosed herein for use in a method for treating an HIV infection in a human having or at risk of having the infection, wherein the compound is administered in combination with one or more (e.g., one, two, three, one or two, or one to three) additional therapeutic agents. In certain embodiments, the present invention provides a compound disclosed herein in combination with one or more additional therapeutic agents which are suitable for treating an HIV infection, for use in a method for treating an HIV infection. In certain embodiments, the present invention provides a compound disclosed herein for use in a method for treating an HIV infection, wherein the compound is administered in combination with one or more additional therapeutic agents which are suitable for treating an HIV infection.

One embodiment provides the use of a compound disclosed herein thereof, in combination with one or more (e.g., one, two, three, one or two, or one to three) additional therapeutic agents in the manufacture of a medicament for treating or preventing an HIV infection in a human having or at risk of having the infection. One embodiment provides the use of a compound disclosed herein in combination with one or more (e.g., one, two, three, one or two, or one to three) additional therapeutic agents in the manufacture of a medicament for treating an HIV infection in a human having or at risk of having the infection. One embodiment provides the use of a compound disclosed herein in the manufacture of a medicament for treating or preventing an HIV infection in a human having or at risk of having the infection, wherein the compound is administered in combination with one or more (e.g., one, two, three, one or two, or one to three) additional therapeutic agents. One embodiment provides the use of a compound disclosed herein thereof, in the manufacture of a medicament for treating an HIV infection in a human having or at risk of having the infection, wherein the compound is administered in combination with one or more (e.g., one, two, three, one or two, or one to three) additional therapeutic agents. In certain embodiments, the present invention provides the use of a compound disclosed herein thereof, in combination with one or more additional therapeutic agents which are suitable for treating an HIV infection, in treating an HIV infection. In certain embodiments, the present invention provides the use of a compound disclosed herein thereof for treating an HIV infection, wherein the compound is administered in combination with one or more additional therapeutic agents which are suitable for treating an HIV infection.

A compound as disclosed herein (e.g., any compound of Formula (II)) may be combined with one or more additional therapeutic agents in any dosage amount of the compound of Formula II (e.g., from 50 mg to 1000 mg of compound).

In one embodiment, pharmaceutical compositions comprising a compound disclosed herein in combination with one or more (e.g., one, two, three, one or two, or one to three) additional therapeutic agents, and a pharmaceutically acceptable carrier, diluent or excipient are provided.

In one embodiment, combination pharmaceutical agents comprising a compound disclosed herein in combination with one or more (e.g., one, two, three, one or two, or one to three) additional therapeutic agents are provided.

In one embodiment, kits comprising a compound disclosed herein in combination with one or more (e.g., one, two, three, one or two, or one to three) additional therapeutic agents are provided.

In the above embodiments, the additional therapeutic agent may be an anti-HIV agent. For example, in some embodiments, the additional therapeutic agent is selected from the group consisting of HIV protease inhibitors, HIV non-nucleoside inhibitors of reverse transcriptase, HIV nucleoside or nucleotide inhibitors of reverse transcriptase, HIV integrase inhibitors, HIV non-catalytic site (or allosteric) integrase inhibitors, entry inhibitors (e.g., CCR5 inhibitors, gp41 inhibitors (i.e., fusion inhibitors) and CD4 attachment inhibitors), CXCR4 inhibitors, gp120 inhibitors, G6PD and NADH-oxidase inhibitors, compounds that target the HIV capsid ("capsid inhibitors"; e.g., capsid polymerization inhibitors or capsid disrupting compounds such as those disclosed in WO 2013/006738 (Gilead Sciences), US 2013/0165489 (University of Pennsylvania), and WO 2013/006792 (Pharma Resources), pharmacokinetic enhancers, and other drugs for treating HIV, and combinations thereof.

In other embodiments, the additional therapeutic agent may be an anti-HIV agent. For example, in some embodiments, the additional therapeutic agent is selected from the group consisting of HIV protease inhibitors, HIV non-nucleoside or non-nucleotide inhibitors of reverse transcriptase, HIV nucleoside or nucleotide inhibitors of reverse transcriptase, HIV integrase inhibitors, HIV non-catalytic site (or allosteric) integrase inhibitors, HIV entry inhibitors (e.g., CCR5 inhibitors, gp41 inhibitors (i.e., fusion inhibitors) and CD4 attachment inhibitors), CXCR4 inhibitors, gp120 inhibitors, G6PD and NADH-oxidase inhibitors, HIV vaccines, HIV maturation inhibitors, latency reversing agents (e.g., histone deacetylase inhibitors, proteasome inhibitors, protein kinase C (PKC) activators, and BRD4 inhibitors), compounds that target the HIV capsid ("capsid inhibitors"; e.g., capsid polymerization inhibitors or capsid disrupting compounds, HIV nucleocapsid p7 (NCp7) inhibitors, HIV p24 capsid protein inhibitors), pharmacokinetic enhancers, immune-based therapies (e.g., Pd-1 modulators, Pd-L1 modulators, toll like receptors modulators, IL-15 agonists,), HIV antibodies, bispecific antibodies and "antibody-like" therapeutic proteins (e.g., DARTs®, Duobodies®, Bites®, XmAbs®, TandAbs®, Fab derivatives) including those targeting HIV gp120 or gp41, combination drugs for HIV, HIV p17 matrix protein inhibitors, IL-13 antagonists, Peptidyl-prolyl cis-trans isomerase A modulators, Protein disulfide isomerase inhibitors, Complement C5a receptor antagonists, DNA methyltransferase inhibitor, HIV vif gene modulators, Vif dimerization antagonists, HIV-1 viral infectivity factor inhibitors, TAT protein inhibitors, HIV-1 Nef modulators, Hck tyrosine kinase modulators, mixed lineage kinase-3 (MLK-3) inhibitors, HIV-1 splicing inhibitors, Rev protein inhibitors, Integrin antagonists, Nucleoprotein inhibitors, Splicing factor modulators, COMM domain containing protein 1 modulators, HIV Ribonuclease H inhibitors, Retrocyclin modulators, CDK-9 inhibitors, Dendritic ICAM-3 grabbing nonintegrin 1 inhibitors, HIV GAG protein inhibitors, HIV POL protein inhibitors, Complement Factor H modulators, Ubiquitin ligase inhibitors, Deoxycytidine kinase inhibitors, Cyclin dependent kinase inhibitors Proprotein convertase PC9 stimulators, ATP dependent RNA helicase DDX3X inhibitors, reverse transcriptase priming complex inhibitors, HIV gene therapy, PI3K inhibitors, compounds such as those disclosed in WO 2013/006738 (Gilead Sciences), US 2013/0165489 (University of Pennsylvania), WO 2013/091096A1 (Boehringer Ingelheim), WO 2009/062285 (Boehringer Ingelheim), US20140221380 (Japan Tobacco), US20140221378 (Japan Tobacco), WO 2010/130034 (Boehringer Ingelheim), WO 2013/159064 (Gilead Sciences), WO 2012/145728 (Gilead Sciences), WO2012/003497 (Gilead Sciences), WO2014/100323 (Gilead Sciences), WO2012/145728 (Gilead Sciences), WO2013/159064 (Gilead Sciences) and WO 2012/003498 (Gilead Sciences) and WO 2013/006792 (Pharma Resources), and other drugs for treating HIV, and combinations thereof.

In certain embodiments, the additional therapeutic is selected from the group consisting of HIV protease inhibitors, HIV non-nucleoside or non-nucleotide inhibitors of reverse transcriptase, HIV nucleoside or nucleotide inhibitors of reverse transcriptase, HIV integrase inhibitors, HIV non-catalytic site (or allosteric) integrase inhibitors, pharmacokinetic enhancers, and combinations thereof.

In certain embodiments a compound of Formula (II) is formulated as a tablet, which may optionally contain one or more other compounds useful for treating HIV. In certain embodiments, the tablet can contain another active ingredient for treating HIV, such as HIV protease inhibitors, HIV non-nucleoside or non-nucleotide inhibitors of reverse transcriptase, HIV nucleoside or nucleotide inhibitors of reverse transcriptase, HIV integrase inhibitors, HIV non-catalytic site (or allosteric) integrase inhibitors, pharmacokinetic enhancers, and combinations thereof. In certain embodiments, the tablet can contain one or more active ingredients for treating HIV, such as HIV nucleoside or nucleotide inhibitors of reverse transcriptase. In certain embodiments, such tablets are suitable for once daily dosing.

In further embodiments, the additional therapeutic agent is selected from one or more of:

(1) HIV protease inhibitors selected from the group consisting of amprenavir, atazanavir, fosamprenavir, indinavir, lopinavir, ritonavir, nelfinavir, saquinavir, tipranavir, brecanavir, darunavir, TMC-126, TMC-114, mozenavir (DMP-450), JE-2147 (AG1776), L-756423, R00334649, KNI-272, DPC-681, DPC-684, GW640385X, DG17, PPL-100, DG35, and AG 1859;

(2) HIV non-nucleoside or non-nucleotide inhibitors of reverse transcriptase selected from the group consisting of capravirine, emivirine, delaviridine, efavirenz, nevirapine, (+) calanolide A, etravirine, GW5634, DPC-083, DPC-961, DPC-963, MIV-150, TMC-120, rilpivirine, BILR 355 BS, VRX 840773, lersivirine (UK-453061), RDEA806, KMO23 and MK-1439;

(3) HIV nucleoside or nucleotide inhibitors of reverse transcriptase selected from the group consisting of zidovudine, emtricitabine, didanosine, stavudine, zalcitabine, lamivudine, abacavir, abacavir sulfate, amdoxovir, elvucitabine, alovudine, MIV-210, ±-FTC, D-d4FC, emtricitabine, phosphazide, fozivudine tidoxil, apricitibine (AVX754), KP-1461, GS-9131 (Gilead Sciences), fosalvudine tidoxil (formerly HDP 99.0003), tenofovir, tenofovir disoproxil fumarate, tenofovir alafenamide, tenofovir alafenamide hemifumarate, tenofovir alafenamide fumarate (Gilead Sciences), GS-7340 (Gilead Sciences), GS-9148 (Gilead Sciences), adefovir, adefovir dipivoxil, CMX-001 (Chimerix) and CMX-157 (Chimerix);

(4) HIV integrase inhibitors selected from the group consisting of curcumin, derivatives of curcumin, chicoric acid, derivatives of chicoric acid, 3,5-dicaffeoylquinic acid, derivatives of 3,5-dicaffeoylquinic acid, aurintricarboxylic acid, derivatives of aurintricarboxylic acid, caffeic acid phenethyl ester, derivatives of caffeic acid phenethyl ester, tyrphostin, derivatives of tyrphostin, quercetin, derivatives of quercetin, S-1360, AR-177, L-870812, and L-870810, raltegravir, BMS-538158, GSK364735C, BMS-707035, MK-2048, BA 011, elvitegravir, dolutegravir, dolutegravir sodium, and GSK-744;

(6) HIV non-catalytic site, or allosteric, integrase inhibitors (NCINI) including, but not limited to, BI-224436, CX0516, CX05045, CX14442, compounds disclosed in WO 2009/062285 (Boehringer Ingelheim), WO 2010/130034 (Boehringer Ingelheim), WO 2013/159064 (Gilead Sciences), WO 2012/145728 (Gilead Sciences), WO 2012/003497 (Gilead Sciences), WO 2012/003498 (Gilead Sciences) each of which is incorporated by references in its entirety herein;

(7) gp41 inhibitors selected from the group consisting of enfuvirtide, sifuvirtide, albuvirtide, FB006M, and TRI-1144;

(8) the CXCR4 inhibitor AMD-070;

(9) the entry inhibitor SP01A;

(10) the gp120 inhibitor BMS-488043;

(11) the G6PD and NADH-oxidase inhibitor immunitin;

(12) CCR5 inhibitors selected from the group consisting of aplaviroc, vicriviroc, maraviroc, cenicriviroc, PRO-140, INCB15050, PF-232798 (Pfizer), and CCR5mAb004;

(13) CD4 attachment inhibitors selected from the group consisting of ibalizumab (TMB-355) and BMS-068 (BMS-663068);

(14) pharmacokinetic enhancers selected from the group consisting of cobicistat and SPI-452; and

(15) other drugs for treating HIV selected from the group consisting of BAS-100, SPI-452, REP 9, SP-01A, TNX-355, DES6, ODN-93, ODN-112, VGV-1, PA-457 (bevirimat), HRG214, VGX-410, KD-247, AMZ 0026, CYT 99007A-221 HIV, DEBIO-025, BAY 50-4798, MDX010 (ipilimumab), PBS 119, ALG 889, and PA-1050040 (PA-040), and combinations thereof.

In certain embodiments, the additional therapeutic agent is selected from one or more of:

(1) Combination drugs selected from the group consisting of ATRIPLA® (efavirenz+tenofovir disoproxil fumarate+emtricitabine), COMPLERA® or EVIPLERA® (rilpivirine+tenofovir disoproxil fumarate+emtricitabine), STRIBILD® (elvitegravir+cobicistat+tenofovir disoproxil fumarate+emtricitabine), dolutegravir+abacavir sulfate+lamivudine, TRIUMEQ® (dolutegravir+abacavir+lamivudine), lamivudine+nevirapine+zidovudine, dolutegravir+rilpivirine, dolutegravir+rilpivirine hydrochloride, atazanavir sulfate+cobicistat, atazanavir+cobicistat, darunavir+cobicistat, efavirenz+lamivudine+tenofovir disoproxil fumarate, tenofovir alafenamide hemifumarate+emtricitabine+cobicistat+elvitegravir, tenofovir alafenamide hemifumarate+emtricitabine, tenofovir alafenamide+emtricitabine, tenofovir alafenamide hemifumarate+emtricitabine+rilpivirine, tenofovir alafenamide+emtricitabine+rilpivirine, Vacc-4x+romidepsin, darunavir+tenofovir alafenamide hemifumarate+emtricitabine+cobicistat, APH-0812, raltegravir+lamivudine, KALETRA® (ALUVIA®, lopinavir+ritonavir), atazanavir sulfate+ritonavir, COMBIVIR® (zidovudine+lamivudine, AZT+3TC), EPZICOM® (Kivexa®, abacavir sulfate+lamivudine, ABC+3TC), TRIZIVIR® (abacavir sulfate+zidovudine+lamivudine, ABC+AZT+3TC), TRUVADA® (tenofovir disoproxil fumarate+emtricitabine, TDF+FTC), doravirine+lamivudine+tenofovir disoproxil fumarate, doravirine+lamivudine+tenofovir disoproxil, tenofovir+lamivudine and lamivudine+tenofovir disoproxil fumarate;

(2) HIV protease inhibitors selected from the group consisting of amprenavir, atazanavir, fosamprenavir, fosamprenavir calcium, indinavir, indinavir sulfate, lopinavir, ritonavir, nelfinavir, nelfinavir mesylate, saquinavir, saquinavir mesylate, tipranavir, brecanavir, darunavir, DG-17, TMB-657 (PPL-100) and TMC-310911;

(3) HIV non-nucleoside or non-nucleotide inhibitors of reverse transcriptase selected from the group consisting of delavirdine, delavirdine mesylate, nevirapine, etravirine, dapivirine, doravirine, rilpivirine, efavirenz, KM-023, VM-1500, lentinan and AIC-292;

(4) HIV nucleoside or nucleotide inhibitors of reverse transcriptase selected from the group consisting of VIDEX® and VIDEX® EC (didanosine, ddI), zidovudine, emtricitabine, didanosine, stavudine, zalcitabine, lamivudine, censavudine, abacavir, abacavir sulfate, amdoxovir, elvucitabine, alovudine, phosphazid, fozivudine tidoxil, apricitabine, amdoxovir, KP-1461, fosalvudine tidoxil, tenofovir, tenofovir disoproxil, tenofovir disoproxil fumarate, tenofovir disoproxil hemifumarate, tenofovir alafenamide, tenofovir alafenamide hemifumarate, tenofovir alafenamide fumarate, adefovir, adefovir dipivoxil, and festinavir;

(5) HIV integrase inhibitors selected from the group consisting of curcumin, derivatives of curcumin, chicoric acid, derivatives of chicoric acid, 3,5-dicaffeoylquinic acid, derivatives of 3,5-dicaffeoylquinic acid, aurintricarboxylic acid, derivatives of aurintricarboxylic acid, caffeic acid phenethyl ester, derivatives of caffeic acid phenethyl ester, tyrphostin, derivatives of tyrphostin, quercetin, derivatives of quercetin, raltegravir, elvitegravir, dolutegravir and cabotegravir;

(6) HIV non-catalytic site, or allosteric, integrase inhibitors (NCINI) selected from the group consisting of CX-05168, CX-05045 and CX-14442;

(7) HIV gp41 inhibitors selected from the group consisting of enfuvirtide, sifuvirtide and albuvirtide;

(8) HIV entry inhibitors selected from the group consisting of cenicriviroc;

(9) HIV gp120 inhibitors selected from the group consisting of Radha-108 (Receptol) and BMS-663068;

(10) CCR5 inhibitors selected from the group consisting of aplaviroc, vicriviroc, maraviroc, cenicriviroc, PRO-140, Adaptavir (RAP-101), nifeviroc (TD-0232), TD-0680, and vMIP (Haimipu);

(11) CD4 attachment inhibitors selected from the group consisting of ibalizumab;

(12) CXCR4 inhibitors selected from the group consisting of plerixafor, ALT-1188, vMIP and Haimipu;

(13) Pharmacokinetic enhancers selected from the group consisting of cobicistat and ritonavir;

(14) Immune-based therapies selected from the group consisting of dermaVir, interleukin-7, plaquenil (hydroxychloroquine), proleukin (aldesleukin, IL-2), interferon alfa, interferon alfa-2b, interferon alfa-n3, pegylated interferon alfa, interferon gamma, hydroxyurea, mycophenolate mofetil (MPA) and its ester derivative mycophenolate mofetil (MMF), WF-10, ribavirin, IL-2, IL-12, polymer polyethyleneimine (PEI), Gepon, VGV-1, MOR-22, BMS-936559, toll-like receptors modulators (tlr1, tlr2, tlr3, tlr4, tlr5, tlr6, tlr7, tlr8, tlr9, tlr10, tlr11, tlr12 and tlr13), rintatolimod and IR-103;

(15) HIV vaccines selected from the group consisting of peptide vaccines, recombinant subunit protein vaccines, live vector vaccines, DNA vaccines, virus-like particle vaccines (pseudovirion vaccine), CD4-derived peptide vaccines, vaccine combinations, rgp 120 (AIDSVAX), ALVAC HIV (vCP1521)/AIDSVAX B/E (gp120) (RV144), monomeric gp120 HIV-1 subtype C vaccine (Novartis), Remune, ITV-1, Contre Vir, Ad5-

ENVA-48, DCVax-001 (CDX-2401), PEP-6409, Vacc-4x, Vacc-05, VAC-3S, multiclade DNA recombinant adenovirus-5 (rAd5), Pennvax-G, VRC-HIV MAB060-00-AB, AVX-101, Tat Oyi vaccine, AVX-201, HIV-LAMP-vax, Ad35, Ad35-GRIN, NAcGM3/VSSP ISA-51, poly-ICLC adjuvanted vaccines, TatImmune, GTU-multiHIV (FIT-06), AGS-004, gp140[delta]V2.TV1+MF-59, rVSVIN HIV-1 gag vaccine, SeV-Gag vaccine, AT-20, DNK-4, Ad35-GRIN/ENV, TBC-M4, HIVAX, HIVAX-2, NYVAC-HIV-PT1, NYVAC-HIV-PT4, DNA-HIV-PT123, rAAV1-PG9DP, GOVX-B11, GOVX-B21, Thy-01, TUTI-16, VGX-3300, TVI-HIV-1, Ad-4 (Ad4-env Clade C+Ad4-mGag), EN41-UGR7C, EN41-FPA2, PreVaxTat, TL-01, SAV-001, AE-H, MYM-V101, CombiHIVvac, ADVAX, MYM-V201, MVA-CMDR, ETV-01, CDX-1401, rcAd26.MOS1.HIV-Env and DNA-Ad5 gag/pol/nef/nev (HVTN505);

(16) HIV antibodies, bispecific antibodies and "antibody-like" therapeutic proteins (such as DARTs®, Duobodies®, Bites®, XmAbs®, TandAbs®, Fab derivatives) including BMS-936559, TMB-360 and those targeting HIV gp120 or gp41 selected from the group consisting of bavituximab, UB-421, C2F5, C2G12, C4E10, C2F5+C2G12+C4E10, 3-BNC-117, PGT145, PGT121, MDX010 (ipilimumab), VRC01, A32, 7B2, 10E8, VRC-07-523 and VRC07;

(17) latency reversing agents selected from the group consisting of Histone deacetylase inhibitors such as Romidepsin, vorinostat, panobinostat; Proteasome inhibitors such as Velcade; protein kinase C (PKC) activators such as Indolactam, Prostratin, Ingenol B and DAG-lactones, Ionomycin, GSK-343, PMA, SAHA, BRD4 inhibitors, IL-15, JQ1, disulfram, and amphotericin B;

(18) HIV nucleocapsid p7 (NCp7) inhibitors selected from the group consisting of azodicarbonamide;

(19) HIV maturation inhibitors selected from the group consisting of BMS-955176 and GSK-2838232;

(20) PI3K inhibitors selected from the group consisting of idelalisib, AZD-8186, buparlisib, CLR-457, pictilisib, neratinib, rigosertib, rigosertib sodium, EN-3342, TGR-1202, alpelisib, duvelisib, UCB-5857, taselisib, XL-765, gedatolisib, VS-5584, copanlisib, CAI orotate, perifosine, RG-7666, GSK-2636771, DS-7423, panulisib, GSK-2269557, GSK-2126458, CUDC-907, PQR-309, INCB-040093, pilaralisib, BAY-1082439, puquitinib mesylate, SAR-245409, AMG-319, RP-6530, ZSTK-474, MLN-1117, SF-1126, RV-1729, sonolisib, LY-3023414, SAR-260301 and CLR-1401;

(21) the compounds disclosed in WO 2004/096286 (Gilead Sciences), WO 2006/110157 (Gilead Sciences), WO 2006/015261 (Gilead Sciences), WO 2013/006738 (Gilead Sciences), US 2013/0165489 (University of Pennsylvania), US20140221380 (Japan Tobacco), US20140221378 (Japan Tobacco), WO 2013/006792 (Pharma Resources), WO 2009/062285 (Boehringer Ingelheim), WO 2010/130034 (Boehringer Ingelheim), WO 2013/091096A1 (Boehringer Ingelheim), WO 2013/159064 (Gilead Sciences), WO 2012/145728 (Gilead Sciences), WO2012/003497 (Gilead Sciences), WO2014/100323 (Gilead Sciences), WO2012/145728 (Gilead Sciences), WO2013/159064 (Gilead Sciences) and WO 2012/003498 (Gilead Sciences); and

(22) other drugs for treating HIV selected from the group consisting of BanLec, MK-8507, AG-1105, TR-452, MK-8591, REP 9, CYT-107, alisporivir, NOV-205, IND-02, metenkefalin, PGN-007, Acemannan, Gamimune, Prolastin, 1,5-dicaffeoylquinic acid, BIT-225, RPI-MN, VSSP, Hlviral, IMO-3100, SB-728-T, RPI-MN, VIR-576, HGTV-43, MK-1376, rHIV7-shl-TAR-CCR5RZ, MazF gene therapy, BlockAide, ABX-464, SCY-635, naltrexone, AAV-eCD4-Ig gene therapy and PA-1050040 (PA-040);

and combinations thereof.

In certain embodiments, a compound disclosed herein is combined with two, three, four or more additional therapeutic agents. In certain embodiments, a compound disclosed herein is combined with two additional therapeutic agents. In other embodiments, a compound disclosed herein is combined with three additional therapeutic agents. In further embodiments, a compound disclosed herein is combined with four additional therapeutic agents. The two, three four or more additional therapeutic agents can be different therapeutic agents selected from the same class of therapeutic agents, or they can be selected from different classes of therapeutic agents. In a specific embodiment, a compound disclosed herein is combined with an HIV nucleoside or nucleotide inhibitor of reverse transcriptase and an HIV non-nucleoside inhibitor of reverse transcriptase. In another specific embodiment, a compound disclosed herein is combined with an HIV nucleoside or nucleotide inhibitor of reverse transcriptase, and an HIV protease inhibiting compound. In a further embodiment, a compound disclosed herein is combined with an HIV nucleoside or nucleotide inhibitor of reverse transcriptase, an HIV non-nucleoside inhibitor of reverse transcriptase, and an HIV protease inhibiting compound. In an additional embodiment, a compound disclosed herein is combined with an HIV nucleoside or nucleotide inhibitor of reverse transcriptase, an HIV non-nucleoside inhibitor of reverse transcriptase, and a pharmacokinetic enhancer. In another embodiment, a compound disclosed herein is combined with two HIV nucleoside or nucleotide inhibitors of reverse transcriptase.

In certain embodiments, a compound disclosed herein, is combined with one, two, three, four or more additional therapeutic agents. In certain embodiments, a compound disclosed herein is combined with one additional therapeutic agent. In certain embodiments, a compound disclosed herein is combined with two additional therapeutic agents. In other embodiments, a compound disclosed herein is combined with three additional therapeutic agents. In further embodiments, a compound disclosed herein is combined with four additional therapeutic agents. The one, two, three, four or more additional therapeutic agents can be different therapeutic agents selected from the same class of therapeutic agents, and/or they can be selected from different classes of therapeutic agents. In a specific embodiment, a compound disclosed herein is combined with an HIV nucleoside or nucleotide inhibitor of reverse transcriptase and an HIV non-nucleoside inhibitor of reverse transcriptase. In another specific embodiment, a compound disclosed herein is combined with an HIV nucleoside or nucleotide inhibitor of reverse transcriptase, and an HIV protease inhibiting compound. In a further embodiment, a compound disclosed herein is combined with an HIV nucleoside or nucleotide inhibitor of reverse transcriptase, an HIV non-nucleoside inhibitor of reverse transcriptase, and an HIV protease inhibiting compound. In an additional embodiment, a compound disclosed herein is combined with an HIV nucleoside or nucleotide inhibitor of reverse transcriptase, an HIV non-nucleoside inhibitor of reverse transcriptase, and a pharmacokinetic enhancer. In certain embodiments, a compound disclosed herein is combined with at least one HIV nucleoside inhibitor of reverse transcriptase, an integrase inhibitor, and a pharmacokinetic enhancer. In another embodiment, a compound disclosed herein is combined with two HIV nucleoside or nucleotide inhibitors of reverse transcriptase.

In certain embodiments, a compound disclosed herein is combined with at least one HIV nucleoside inhibitor of reverse transcriptase, an integrase inhibitor, and a pharmacokinetic enhancer.

In a particular embodiment, a compound disclosed herein is combined with abacavir, abacavir sulfate, tenofovir, tenofovir disoproxil fumarate, tenofovir alafenamide, or tenofovir alafenamide hemifumarate.

In a particular embodiment, a compound disclosed herein is combined with tenofovir, tenofovir disoproxil fumarate, tenofovir alafenamide, or tenofovir alafenamide hemifumarate.

In a particular embodiment, a compound disclosed herein is combined with a first additional therapeutic agent selected from the group consisting of: abacavir, abacavir sulfate, tenofovir, tenofovir disoproxil fumarate, tenofovir alafenamide, and tenofovir alafenamide hemifumarate and a second additional therapeutic agent selected from the group consisting of emtricitibine and lamivudine.

In a particular embodiment, a compound disclosed herein is combined with a first additional therapeutic agent selected from the group consisting of: tenofovir, tenofovir disoproxil fumarate, tenofovir alafenamide, and tenofovir alafenamide hemifumarate and a second additional therapeutic agent, wherein the second additional therapeutic agent is emtricitibine.

In a particular embodiment, a compound disclosed herein is combined with one, two, three, four or more additional therapeutic agents selected from Triumeq® (dolutegravir+abacavir+lamivudine), dolutegravir+abacavir sulfate+lamivudine, raltegravir, raltegravir+lamivudine, Truvada® (tenofovir disoproxil fumarate+emtricitabine, TDF+FTC), maraviroc, enfuvirtide, Epzicom® (Livexa®, abacavir sulfate+lamivudine, ABC+3TC), Trizivir® (abacavir sulfate+zidovudine+lamivudine, ABC+AZT+3TC), adefovir, adefovir dipivoxil, Stribild® (elvitegravir+cobicistat+tenofovir disoproxil fumarate+emtricitabine), rilpivirine, rilpivirine hydrochloride, Complera® (Eviplera®, rilpivirine+tenofovir disoproxil fumarate+emtricitabine), Cobicistat, atazanavir sulfate+cobicistat, atazanavir+cobicistat, darunavir+cobicistat, Atripla® (efavirenz+tenofovir disoproxil fumarate+emtricitabine), atazanavir, atazanavir sulfate, dolutegravir, elvitegravir, Aluvia® (Kaletra®, lopinavir+ritonavir), ritonavir, emtricitabine, atazanavir sulfate+ritonavir, darunavir, lamivudine, Prolastin, fosamprenavir, fosamprenavir calcium, efavirenz, Combivir® (zidovudine+lamivudine, AZT+3TC), etravirine, nelfinavir, nelfinavir mesylate, interferon, didanosine, stavudine, indinavir, indinavir sulfate, tenofovir+lamivudine, zidovudine, nevirapine, saquinavir, saquinavir mesylate, aldesleukin, zalcitabine, tipranavir, amprenavir, delavirdine, delavirdine mesylate, Radha-108 (Receptol), Hlviral, lamivudine+tenofovir disoproxil fumarate, efavirenz+lamivudine+tenofovir disoproxil fumarate, phosphazid, lamivudine+nevirapine+zidovudine, abacavir, abacavir sulfate, tenofovir, tenofovir disoproxil, tenofovir disoproxil fumarate, darunavir+cobicistat, atazanavir sulfate+cobicistat, atazanavir+cobicistat, tenofovir alafenamide and tenofovir alafenamide hemifumarate.

In a particular embodiment, a compound disclosed herein is combined with abacavir, abacavir sulfate, tenofovir, tenofovir disoproxil, tenofovir disoproxil fumarate, tenofovir disoproxil hemifumarate, tenofovir alafenamide or tenofovir alafenamide hemifumarate.

In a particular embodiment, a compound disclosed herein is combined with tenofovir, tenofovir disoproxil, tenofovir disoproxil fumarate, tenofovir alafenamide, or tenofovir alafenamide hemifumarate.

In a particular embodiment, a compound disclosed herein is combined with a first additional therapeutic agent selected from the group consisting of: abacavir sulfate, tenofovir, tenofovir disoproxil, tenofovir disoproxil fumarate, tenofovir alafenamide, and tenofovir alafenamide hemifumarate and a second additional therapeutic agent selected from the group consisting of emtricitabine and lamivudine.

In a particular embodiment, a compound disclosed herein is combined with a first additional therapeutic agent selected from the group consisting of: tenofovir, tenofovir disoproxil, tenofovir disoproxil fumarate, tenofovir alafenamide, and tenofovir alafenamide hemifumarate and a second additional therapeutic agent, wherein the second additional therapeutic agent is emtricitabine.

In certain embodiments, a compound disclosed herein is combined with 5-30 mg tenofovir alafenamide fumarate, tenofovir alafenamide hemifumarate, or tenofovir alafenamide and 200 mg emtricitabine. In certain embodiments, a compound disclosed herein is combined with 5-10; 5-15; 5-20; 5-25; 25-30; 20-30; 15-30; or 10-30 mg tenofovir alafenamide fumarate, tenofovir alafenamide hemifumarate, or tenofovir alafenamide and 200 mg emtricitabine. In certain embodiments, a compound disclosed herein is combined with 10 mg tenofovir alafenamide fumarate, tenofovir alafenamide hemifumarate, or tenofovir alafenamide and 200 mg emtricitabine. In certain embodiments, a compound disclosed herein is combined with 25 mg tenofovir alafenamide fumarate, tenofovir alafenamide hemifumarate, or tenofovir alafenamide and 200 mg emtricitabine. A compound as disclosed herein (e.g., a compound of formula (II)) may be combined with the agents provided herein in any dosage amount of the compound (e.g., from 50 mg to 500 mg of compound) the same as if each combination of dosages were specifically and individually listed.

In certain embodiments, a compound disclosed herein is combined with 200-400 mg tenofovir disproxil, tenofovir disoproxil fumarate, or tenofovir disoproxil hemifumarate and 200 mg emtricitabine. In certain embodiments, a compound disclosed herein is combined with 200-250; 200-300; 200-350; 250-350; 250-400; 350-400; 300-400; or 250-400 mg tenofovir disoproxil, tenofovir disoproxil fumarate, or tenofovir disoproxil hemifumarate and 200 mg emtricitabine. In certain embodiments, a compound disclosed herein is combined with 300 mg tenofovir disoproxil fumarate, tenofovir disoproxil hemifumarate, or tenofovir disoproxil and 200 mg emtricitabine. A compound as disclosed herein (e.g., a compound of formula (II)) may be combined with the agents provided herein in any dosage amount of the compound (e.g., from 50 mg to 500 mg of compound) the same as if each combination of dosages were specifically and individually listed.

In certain embodiments, when a compound disclosed herein is combined with one or more additional therapeutic agents as described above, the components of the composition are administered as a simultaneous or sequential regimen. When administered sequentially, the combination may be administered in two or more administrations.

In certain embodiments, a compound disclosed herein is combined with one or more additional therapeutic agents in a unitary dosage form for simultaneous administration to a patient, for example as a solid dosage form for oral administration.

In certain embodiments, a compound disclosed herein is administered with one or more additional therapeutic agents. Co-administration of a compound disclosed herein with one or more additional therapeutic agents generally refers to simultaneous or sequential administration of a compound disclosed herein and one or more additional therapeutic agents, such that therapeutically effective amounts of the compound disclosed herein and one or more additional therapeutic agents are both present in the body of the patient.

Co-administration includes administration of unit dosages of the compounds disclosed herein before or after administration of unit dosages of one or more additional therapeutic agents, for example, administration of the compound disclosed herein within seconds, minutes, or hours of the administration of one or more additional therapeutic agents. For example, in some embodiments, a unit dose of a compound disclosed herein is administered first, followed within seconds or minutes by administration of a unit dose of one or more additional therapeutic agents. Alternatively, in other embodiments, a unit dose of one or more additional therapeutic agents is administered first, followed by administration of a unit dose of a compound disclosed herein within seconds or minutes. In some embodiments, a unit dose of a compound disclosed herein is administered first, followed, after a period of hours (e.g., 1-12 hours), by administration of a unit dose of one or more additional therapeutic agents. In other embodiments, a unit dose of one or more additional therapeutic agents is administered first, followed, after a period of hours (e.g., 1-12 hours), by administration of a unit dose of a compound disclosed herein.

XRPD Data

In certain embodiments, the crystalline forms are characterized by the interlattice plane intervals determined by an X-ray powder diffraction pattern (XRPD). The diffractogram of XRPD is typically represented by a diagram plotting the intensity of the peaks versus the location of the peaks, i.e., diffraction angle 2θ (two-theta) in degrees. The intensities are often given in parenthesis with the following abbreviations: very strong=vst; strong=st; medium=m; weak=w; and very weak=vw. The characteristic peaks of a given XRPD can be selected according to the peak locations and their relative intensity to conveniently distinguish this crystalline structure from others.

Those skilled in the art recognize that the measurements of the XRPD peak locations and/or intensity for a given crystalline form of the same compound will vary within a margin of error. The values of degree 2θ allow appropriate error margins. Typically, the error margins are represented by "±". For example, the degree 2θ of about "8.7±0.3" denotes a range from about 8.7+0.3, i.e., about 9.0, to about 8.7-0.3, i.e., about 8.4. Depending on the sample preparation techniques, the calibration techniques applied to the instruments, human operational variation, and etc, those skilled in the art recognize that the appropriate error of margins for a XRPD can be ±0.5; ±0.4; ±0.3; ±0.2; ±0.1; ±0.05; or less. In certain embodiments of the invention, the XRPD margin of error is ±0.2.

Additional details of the methods and equipment used for the XRPD analysis are described in the Examples section.

The XRPD peaks for the crystalline forms of sodium (2R,5S,13aR)-7,9-dioxo-10-((2,4,6-trifluorobenzyl)carbamoyl)-2,3,4,5,7,9,13,13a-octahydro-2,5-methanopyrido[1',2': 4,5]pyrazino[2,1-b][1,3]oxazepin-8-olate (Formula II) of the present invention can be found below in Table 1

TABLE 1

XRPD peaks for crystalline forms of Formula II Form I
Formula II
Form I

| Peak Position [°2θ] | Relative Intensity [%] |
|---|---|
| 5.5 | 100.0 |
| 16.1 | 87.3 |
| 17.9 | 22.4 |
| 19.5 | 38.0 |
| 22.1 | 61.8 |
| 22.5 | 42.2 |
| 23.3 | 60.4 |
| 26.6 | 27.3 |
| 28.5 | 42.9 |

Preparation of the Polymorphs

One method of synthesizing (2R,5S,13aR)-8-hydroxy-7,9-dioxo-N-(2,4,6-trifluorobenzyl)-2,3,4,5,7,9,13,13a-octahydro-2,5-methanopyrido[1',2':4,5]pyrazino[2,1-b][1,3]oxazepine-10-carboxamide (e.g. a compound of Formula (I)) has been previously described in PCT Publication No. WO2014/100323. This reference is hereby incorporated herein by reference in its entirety, and specifically with respect to the synthesis of (2R,5S,13aR)-8-hydroxy-7,9-dioxo-N-(2,4,6-trifluorobenzyl)-2,3,4,5,7,9,13,13a-octahydro-2,5-methanopyrido[1',2':4,5]pyrazino[2,1-b][1,3]oxazepine-10-carboxamide. One method of synthesizing sodium (2R,5S,13aR)-7,9-dioxo-10-((2,4,6-trifluorobenzyl) carbamoyl)-2,3,4,5,7,9,13,13a-octahydro-2,5-methanopyrido[1',2':4,5]pyrazino[2,1-b][1,3]oxazepin-8-olate (e.g. a compound of Formula (II)) is described herein.

For example, in one aspect, provided is a method of producing a composition comprising one or more polymorphs of sodium (2R,5S,13aR)-7,9-dioxo-10-((2,4,6-trifluorobenzyl)carbamoyl)-2,3,4,5,7,9,13,13a-octahydro-2,5-methanopyrido[1',2':4,5]pyrazino[2,1-b][1,3]oxazepin-8-olate, wherein the method comprises combining a compound of Formula (II) with a suitable solvent or a mixture of suitable solvents to produce a composition comprising one or more polymorphs of the compound of Formula (II). In another aspect, provided is another method of producing a composition comprising one or more polymorphs of sodium (2R,5S,13aR)-7,9-dioxo-10-((2,4,6-trifluorobenzyl)carbamoyl)-2,3,4,5,7,9,13,13a-octahydro-2,5-methanopyrido[1',2':4,5]pyrazino[2,1-b][1,3]oxazepin-8-olate, wherein the method comprises combining sodium (2R,5S,13aR)-7,9-dioxo-10-((2,4,6-trifluorobenzyl)carbamoyl)-2,3,4,5,7,9,13,13a-octahydro-2,5-methanopyrido[1',2': 4,5]pyrazino[2,1-b][1,3]oxazepin-8-olate with a suitable solvent or a mixture of suitable solvents.

The choice of a particular solvent or combination of solvents affects the formation favoring one polymorphic form of sodium (2R,5S,13aR)-7,9-dioxo-10-((2,4,6-trifluorobenzyl)carbamoyl)-2,3,4,5,7,9,13,13a-octahydro-2,5-methanopyrido[1',2':4,5]pyrazino[2,1-b][1,3]oxazepin-8-olate over another. Solvents suitable for polymorph formation may include, for example, methanol, ethanol, water, isopropyl acetate, acetonitrile, tetrahydrofuran, methyl isobutyl ketone, and any mixtures thereof.

In another aspect, provided is also one or more polymorphs of sodium (2R,5S,13aR)-7,9-dioxo-10-((2,4,6-trifluorobenzyl)carbamoyl)-2,3,4,5,7,9,13,13a-octahydro-2,5- methanopyrido[1',2':4,5]pyrazino[2,1-b][1,3]oxazepin-8-olate produced according to any of the methods described herein.

It should be understood that the methods for preparing the polymorphs described herein (including any polymorphic Form I) may yield quantity and quality differences compared to the methods for preparing sodium (2R,5S,13aR)-7,9-dioxo-10-((2,4,6-trifluorobenzyl)carbamoyl)-2,3,4,5,7,9,13,13a-octahydro-2,5-methanopyrido[1',2':4,5]pyrazino[2,1-b][1,3]oxazepin-8-olate produced on laboratory scale.

Formula II, Form I

In one embodiment, provided is a method of producing a composition comprising polymorphic Form I of sodium (2R,5S,13aR)-7,9-dioxo-10-((2,4,6-trifluorobenzyl)carbamoyl)-2,3,4,5,7,9,13,13a-octahydro-2,5-methanopyrido[1',2':4,5]pyrazino[2,1-b][1,3]oxazepin-8-olate, wherein the method comprises combining (2R,5S,13aR)-8-Hydroxy-7,9-dioxo-N-(2,4,6-trifluorobenzyl)-2,3,4,5,7,9,13,13a-octahydro-2,5-methanopyrido[1',2':4,5]pyrazino[2,1-b][1,3]oxazepine-10-carboxamide with a sodium base (e.g. sodium hydroxide) in a solvent to produce a composition comprising polymorphic Form I of sodium (2R,5S,13aR)-7,9-dioxo-10-((2,4,6-trifluorobenzyl)carbamoyl)-2,3,4,5,7,9,13,13a-octahydro-2,5-methanopyrido[1',2':4,5]pyrazino[2,1-b][1,3]oxazepin-8-olate, wherein the solvent is selected from the group consisting of ethanol, dimethylformamide, and any mixture thereof. In an embodiment, the solvent is a mixture of ethanol and dimethylformamide.

Provided is also polymorphic Form I of sodium (2R,5S,13aR)-7,9-dioxo-10-((2,4,6-trifluorobenzyl)carbamoyl)-2,3,4,5,7,9,13,13a-octahydro-2,5-methanopyrido[1',2':4,5]pyrazino[2,1-b][1,3]oxazepin-8-olate prepared by combining (2R,5S,13aR)-8-Hydroxy-7,9-dioxo-N-(2,4,6-trifluorobenzyl)-2,3,4,5,7,9,13,13a-octahydro-2,5-methanopyrido[1',2':4,5]pyrazino[2,1-b][1,3]oxazepine-10-carboxamide with a sodium base (e.g. sodium hydroxide) in a solvent, wherein the solvent is selected from the group consisting of ethanol, dimethylformamide, and any mixture thereof. In an embodiment, the solvent is a mixture of ethanol and dimethylformamide.

Uses in Manufacturing of Drug Product

Formula II

Provided are also a use of the polymorphs described herein in the manufacture of a drug product. The one or more of the polymorphic forms described herein (e.g., polymorphic Form I) may be used as an intermediate in the manufacturing process to produce the drug product.

In certain embodiments, Form I of sodium (2R,5S,13aR)-7,9-dioxo-10-((2,4,6-trifluorobenzyl)carbamoyl)-2,3,4,5,7,9,13,13a-octahydro-2,5-methanopyrido[1',2':4,5]pyrazino[2,1-b][1,3]oxazepin-8-olate are used in the manufacture of an active pharmaceutical ingredient.

Articles of Manufacture and Kits

Compositions comprising one or more of sodium (2R,5S,13aR)-7,9-dioxo-10-((2,4,6-trifluorobenzyl)carbamoyl)-2,3,4,5,7,9,13,13a-octahydro-2,5-methanopyrido[1',2':4,5]pyrazino[2,1-b][1,3]oxazepin-8-olate and formulated in one or more pharmaceutically acceptable carriers, excipients or other ingredients can be prepared, placed in an appropriate container, and labeled for treatment of an indicated condition. Accordingly, there also is contemplated an article of manufacture, such as a container comprising a dosage form of one or more of sodium (2R,5S,13aR)-7,9-dioxo-10-((2,4,6-trifluorobenzyl)carbamoyl)-2,3,4,5,7,9,13,13a-octahydro-2,5-methanopyrido[1',2':4,5]pyrazino[2,1-b][1,3]oxazepin-8-olate, and a label containing instructions for use of the compound(s).

In some embodiments, the article of manufacture is a container comprising a dosage form of sodium (2R,5S,13aR)-7,9-dioxo-10-((2,4,6-trifluorobenzyl)carbamoyl)-2,3,4,5,7,9,13,13a-octahydro-2,5-methanopyrido[1',2':4,5]pyrazino[2,1-b][1,3]oxazepin-8-olate, and one or more pharmaceutically acceptable carriers, excipients or other ingredients. In one embodiment of the articles of manufacture described herein, the dosage form is a tablet.

Kits also are contemplated. For example, a kit can comprise a dosage form of a pharmaceutical composition and a package insert containing instructions for use of the composition in treatment of a medical condition. The instructions for use in the kit may be for treating HIV. In certain embodiments, the instructions for use in the kit may be for treating HIV.

In certain embodiments, the polymorphic and solvate forms described herein may potentially exhibit improved properties. For example, in certain embodiments, the polymorphic and solvate forms described herein may potentially exhibit improved stability. Such improved stability could have a potentially beneficial impact on the manufacture of the Compound of Formula I, such as for example offering the ability to store process intermediate for extended periods of time. Improved stability could also potentially benefit a composition or pharmaceutical composition of the Compound of Formula II. In certain embodiments, the polymorphic and solvate forms described herein may also potentially result in improved yield of the Compound of Formula II, or potentially result in an improvement of the quality of the Compound of Formula II. In certain embodiments, the polymorphic and solvate forms described herein may also exhibit improved pharmacokinetic properties and/or potentially improved bioavailability.

Methods

Synthesis

Sodium (2R,5S,13aR)-7,9-dioxo-10-((2,4,6-trifluorobenzyl)carbamoyl)-2,3,4,5,7,9,13,13a-octahydro-2,5-methanopyrido[1',2':4,5]pyrazino[2,1-b][1, 3]oxazepin-8-olate (Formula II)

(2R,5S,13aR)-8-hydroxy-7,9-dioxo-N-(2,4,6-trifluorobenzyl)-2,3,4,5,7,9,13,13a-octahydro-2,5-methanopyrido[1',2':4,5]pyrazino[2,1-b][1,3]oxazepine-10-carboxamide (20 g) and ethanol (80 mL) were added to a reaction vessel and warmed to about 75° C. Aqueous sodium hydroxide (22 mL 2 M solution) was added over approximately 30 minutes, after which the slurry was cooled to approximately 20° C. over approximately one hour. Sodium (2R,5S,13aR)-7,9-dioxo-10-((2,4,6-trifluorobenzyl)carbamoyl)-2,3,4,5,7,9,13,13a-octahydro-2,5-methanopyrido[1',2':4,5]pyrazino[2,1-b][1,3]oxazepin-8-olate Form I was collected by filtration, washed with EtOH (50 mL) and dried under vacuum.

$^1$H NMR (400 MHz, DMSO-d6) δ 10.63 (t, J=5.8 Hz, 1H), 7.88 (s, 1H), 7.29-7.07 (m, 2H), 5.20 (dd, J=8.6, 3.6 Hz, 1H), 5.09 (t, J=4.1 Hz, 1H), 4.52 (m, 3H), 4.35 (dd, J=12.8, 3.6 Hz, 1H), 3.87 (dd, J=12.7, 8.7 Hz, 1H), 2.03-1.80 (m, 3H), 1.76-1.64 (m, 2H), 1.50-1.40 (m, 1H).

Characterization

Sodium (2R,5S,13aR)-7,9-dioxo-10-((2,4,6-trifluorobenzyl)carbamoyl)-2,3,4,5,7,9,13,13a-octahydro-2,5-methanopyrido[1',2':4,5]pyrazino[2,1-b][1,3]oxazepin-8-olate Form I was characterized by various analytical techniques, including X-ray powder diffraction pattern (XPPD), differential scanning calorimetry (DSC), thermographic analysis (TGA), and dynamic vapor sorption (DVS) using the procedures described below.

X-Ray Powder Diffraction:

XRPD analysis was conducted on a diffractometer (PANanalytical XPERT-PRO, PANanalytical B.V., Almelo, Netherlands) using copper radiation (Cu Kα, λ=1.5418 Å). Samples were prepared for analysis by depositing the powdered sample in the center of an aluminum holder equipped with a zero background plate. The generator was operated at a voltage of 45 kV and amperage of 40 mA. Slits used were Soller 0.02 rad., antiscatter 1.0°, and divergence. The sample rotation speed was 2 sec. Scans were performed from 2 to 40° 2θ during 5-15 min with a step size of 0.0167° 2θ. Data analysis was performed by X'Pert Highscore version 2.2c (PANalytical B.V., Almelo, Netherlands) and X'Pert data viewer version 1.2d (PANalytical B.V., Almelo, Netherlands).

The XRPD pattern for sodium (2R,5S,13aR)-7,9-dioxo-10-((2,4,6-trifluorobenzyl)carbamoyl)-2,3,4,5,7,9,13,13a-octahydro-2,5-methanopyrido[1',2':4,5]pyrazino[2,1-b][1,3]oxazepin-8-olate Form I is represented in FIG. 1. The calculated XRPD pattern for sodium (2R,5S,13aR)-7,9-dioxo-10-((2,4,6-trifluorobenzyl)carbamoyl)-2,3,4,5,7,9,13,13a-octahydro-2,5-methanopyrido[1',2':4,5]pyrazino[2,1-b][1,3]oxazepin-8-olate Form I represented in FIG. 1 was calculated by using Mercury 3.1 Development (Build RC5). Single crystal data for sodium (2R,5S,13aR)-7,9-dioxo-10-((2,4,6-trifluorobenzyl)carbamoyl)-2,3,4,5,7,9,13,13a-octahydro-2,5-methanopyrido[1',2':4,5]pyrazino[2,1-b][1,3]oxazepin-8-olate Form I was input into Mercury 3.1 Development (Build RC5) to calculate the XRPD pattern for sodium (2R,5S,13aR)-7,9-dioxo-10-((2,4,6-trifluorobenzyl)carbamoyl)-2,3,4,5,7,9,13,13a-octahydro-2,5-methanopyrido[1',2':4,5]pyrazino[2,1-b][1,3]oxazepin-8-olate Form I. Bulk material, such as stoichiometry arity between the temperature was obtained on a Rigaku Miniflex II XRD using power settings of 40 kV, 15 mA, scan speed of 2.0000 degrees per minute, a Miniflex 300/600 goniometer and an ASC-6 attachment, a scan range of 3.000 to 40.000 degrees, an incident slit of 1.250 degrees, a length limiting slit of 10.0 mm, and SC-70 detector, a receiving slit #1 of 1.250 degrees, continuous scan mode, and a receiving slit #2 of 0.3 mm. The sample was prepared by smoothing about 20 mg of solids on a silicon disk mounted in a metal holder. Acquisition temperature was ~21° C.

The XRPD pattern for sodium (2R,5S,13aR)-7,9-dioxo-10-((2,4,6-trifluorobenzyl)carbamoyl)-2,3,4,5,7,9,13,13a-octahydro-2,5-methanopyrido[1',2':4,5]pyrazino[2,1-b][1,3]oxazepin-8-olate Form I is further represented in FIG. 8. The calculated XRPD pattern for sodium (2R,5S,13aR)-7,9-dioxo-10-((2,4,6-trifluorobenzyl)carbamoyl)-2,3,4,5,7,9,13,13a-octahydro-2,5-methanopyrido[1',2':4,5]pyrazino[2,1-b][1,3]oxazepin-8-olate Form I represented in FIG. 8 was calculated by using Mercury 3.1 Development (Build RC5). Single crystal data for sodium (2R,5S,13aR)-7,9-dioxo-10-((2,4,6-trifluorobenzyl)carbamoyl)-2,3,4,5,7,9,13,13a-octahydro-2,5-methanopyrido[1',2':4,5]pyrazino[2,1-b][1,3]oxazepin-8-olate Form I was input into Mercury 3.1 Development (Build RC5) to calculate the XRPD pattern for sodium (2R,5S,13aR)-7,9-dioxo-10-((2,4,6-trifluorobenzyl)carbamoyl)-2,3,4,5,7,9,13,13a-octahydro-2,5-methanopyrido[1',2':4,5]pyrazino[2,1-b][1,3]oxazepin-8-olate Form I. Bulk material, such as stoichiometry arity between the temperature was obtained on a Rigaku Miniflex II XRD using power settings of 40 kV, 15 mA, scan speed of 2.0000 degrees per minute, a Miniflex 300/600 goniometer and an ASC-6 attachment, a scan range of 3.000 to 40.000 degrees, an incident slit of 1.250 degrees, a length limiting slit of 10.0 mm, and SC-70 detector, a receiving slit #1 of 1.250 degrees, continuous scan mode, and a receiving slit #2 of 0.3 mm. The sample was prepared by smoothing about 20 mg of solids on a silicon disk mounted in a metal holder. Acquisition temperature was ~21° C.

FIG. 8 compares the calculated XRPD pattern of sodium (2R,5S,13aR)-7,9-dioxo-10-((2,4,6-trifluorobenzyl)carbamoyl)-2,3,4,5,7,9,13,13a-octahydro-2,5-methanopyrido[1',2': 4,5]pyrazino[2,1-b][1,3]oxazepin-8-olate Form I to the experimental XRPD pattern of sodium (2R,5S,13aR)-7,9-dioxo-10-((2,4,6-trifluorobenzyl)carbamoyl)-2,3,4,5,7,9,13, 13a-octahydro-2,5-methanopyrido[1',2':4,5]pyrazino[2,1-b][1,3]oxazepin-8-olate Form I. The comparison shows the degree to which the calculated XRPD and experimental XRPD agree. Strong agreement indicates the solved crystal structure is also the crystal structure of the material analyzed directly by XRPD. This determination can support orthogonal data about the composition of the bulk material, such as stoichiometry.

XRPD peaks are found in Table 1 above.

Differential Scanning Calorimetry:

Thermal properties of sodium (2R,5S,13aR)-7,9-dioxo-10-((2,4,6-trifluorobenzyl)carbamoyl)-2,3,4,5,7,9,13,13a-octahydro-2,5-methanopyrido[1',2':4,5]pyrazino[2,1-b][1,3]oxazepin-8-olate Form I were evaluated using a Differential Scanning calorimetry (DSC) instrument (TA Q1000, TA Instruments, New Castle, Del., USA). Approximately 1 to 10 mg of solid sample was placed in a standard aluminum pan vented with a pinhole for each experiment and heated at a rate of 10° C./min under a 50 mL/min nitrogen purge. Data analysis was conducted using Universal Analysis 2000 Version 4.7A (TA Instruments, New Castle, Del., USA). Heat of fusion analysis was conducted by sigmoidal integration of the endothermic melting peak.

The DSC for sodium (2R,5S,13aR)-7,9-dioxo-10-((2,4,6-trifluorobenzyl)carbamoyl)-2,3,4,5,7,9,13,13a-octahydro-2, 5-methanopyrido[1',2':4,5]pyrazino[2,1-b][1,3]oxazepin-8-olate Form I is represented in FIG. 2.

Thermogravimetric Analysis:

Thermogravimetric analysis (TGA) of sodium (2R,5S, 13aR)-7,9-dioxo-10-((2,4,6-trifluorobenzyl)carbamoyl)-2, 3,4,5,7,9,13,13a-octahydro-2,5-methanopyrido[1',2':4,5] pyrazino[2,1-b][1,3]oxazepin-8-olate Form I was performed on a TGA instrument (TA Q500, TA Instruments, New Castle, Del., USA). Approximately 1 to 10 mg of solid sample was placed in an open aluminum pan for each experiment and heated at a rate of 10° C./min under a 60 mL/min nitrogen purge using. Data analysis was conducted using Universal Analysis 2000 Version 4.7A (TA Instruments, New Castle, Del., USA).

The TGA for sodium (2R,5S,13aR)-7,9-dioxo-10-((2,4,6-trifluorobenzyl)carbamoyl)-2,3,4,5,7,9,13,13a-octahydro-2, 5-methanopyrido[1',2':4,5]pyrazino[2,1-b][1,3]oxazepin-8-olate Form I is represented in FIG. 3.

Dynamic Vapor Sorption:

The hygroscopicity of sodium (2R,5S,13aR)-7,9-dioxo-10-((2,4,6-trifluorobenzyl)carbamoyl)-2,3,4,5,7,9,13,13a-octahydro-2,5-methanopyrido[1',2':4,5]pyrazino[2,1-b][1,3]oxazepin-8-olate Form I was evaluated at about 25° C. using a dynamic vapor sorption (DVS) instrument (TGA Q5000 TA Instruments, New Castle, Del.). Water adsorption and desorption were studied as a function of relative humidity (RH) over the range of 0 to 90% at room temperature. The humidity in the chamber was increased from the initial level 50% RH to 60% RH and held until the solid and atmosphere reached equilibration. The equilibrium test was continued until passed or expired after 10 hours. At this point, RH was raised 10% higher and the process was repeated until 90% RH was reached and equilibrated. During this period, the water sorption was monitored. For desorption, the relative humidity was decreased in a similar manner to measure a full sorption/desorption cycle. The cycle was optionally repeated. All experiments were operated in dm/dt mode (mass variation over time) to determine the equilibration endpoint. Approximately 3 mg of solid sodium (2R,5S,13aR)-7,9-dioxo-10-((2,4,6-trifluorobenzyl)carbamoyl)-2,3,4,5,7,9,13,13a-octahydro-2,5-methanopyrido[1',2':4,5]pyrazino[2,1-b][1,3]oxazepin-8-olate was used. Data analysis was conducted using Universal Analysis 2000 Version 4.7A (TA Instruments, New Castle, Del., USA).

The DVS for sodium (2R,5S,13aR)-7,9-dioxo-10-((2,4,6-trifluorobenzyl)carbamoyl)-2,3,4,5,7,9,13,13a-octahydro-2,5-methanopyrido[1',2':4,5]pyrazino[2,1-b][1,3]oxazepin-8-olate Form I is represented in FIG. 4.

The indexing data for Formula II Form I is summarized in Table 2 below.

TABLE 2

Indexing Data for Formula II Form I

| Form and Identification | Solvent | Unit Cell Dimensions | | | | | |
|---|---|---|---|---|---|---|---|
| | | Distance (Å) | | | Angle (°) | | |
| | | a | b | c | α | β | γ |
| Formula II Form I | methanol | 9.105 | 13.986 | 31.384 | 90 | 90 | 90 |

The single crystal X-ray diffraction studies were carried out on a Bruker APEX II Ultra diffractometer equipped with Mo $K_\alpha$ radiation ($\lambda$=0.71073 Å). Crystals of the subject compound were cut into a 0.22×0.18×0.04 mm section and mounted on a Cryoloop with Paratone-N oil. Data were collected in a nitrogen gas stream at 100 (2) K. A total of 15725 reflections were collected covering the indices, $-9<=h<=10$, $-13<=k<=16$, $-37<=l<=36$. 7163 reflections were found to be symmetry independent, with a $R_{int}$ of 0.0682. Indexing and unit-cell refinement indicated an orthorhombic lattice. The space group, which was uniquely defined by the systematic absences in the data, was found to be $P2_12_12_1$. The data were integrated using the Bruker SAINT software program and scaled using the SADABS software program. Solution by direct methods (SHELXT) produced a complete phasing model compatible with the proposed structure.

All nonhydrogen atoms were refined anisotropically by full-matrix least-squares (SHELXL-2014). All hydrogen atoms were placed using a riding model. Their positions were constrained relative to their parent atom using the appropriate HFIX command in SHELXL-2014. Crystallographic data are summarized in Table 2A. The absolute stereochemistry was set to conform to previously studied samples of the same compound.

The single crystal X-ray crystallography data for Formula II Form I is summarized in Table 2A below.

TABLE 2A

Single Crystal Data for Formula II, Form I

| C42 H34 F6 N6 Na2 O10 | Acquisition Temp. | Space Group P212121 | Z 4 | Unit Cell Dimensions | | | | | |
|---|---|---|---|---|---|---|---|---|---|
| Form and Identification | 100(2) K | Solvent in | Density | Distance (Å) | | | Angle (°) | | |
| | Solvent | lattice | (Mg/m³) | a | b | c | α | β | γ |
| Formula II Form I | Ethanol/ DMF | none | 1.614 | 8.9561 (10) | 13.9202 (14) | 31.115 (3) | 90 | 90 | 90 |

Dissolution Profile

The intrinsic dissolution profile of sodium (2R,5S,13aR)-7,9-dioxo-10-((2,4,6-trifluorobenzyl)carbamoyl)-2,3,4,5,7,9,13,13a-octahydro-2,5-methanopyrido[1',2':4,5]pyrazino[2,1-b][1,3]oxazepin-8-olate (Formula II) Form I of the present invention and the intrinsic dissolution profiles of Form I and Form III of Formula I, the free acid, (2R,5S,13aR)-8-hydroxy-7,9-dioxo-N-(2,4,6-trifluorobenzyl)-2,3,4,5,7,9,13,13a-octahydro-2,5-methanopyrido[1',2':4,5]pyrazino[2,1-b][1,3]oxazepine-10-carboxamide (disclosed in the co-pending U.S. Provisional Application 62/015,238 filed on Jun. 20, 2014 titled CRYSTALLINE FORMS OF (2R,5S,13AR)-8-HYDROXY-7,9-DIOXO-N-(2,4,6-TRIFLUOROBENZYL)-2,3,4,5,7,9,13,13A-OCTAHYDRO-2,5-METHANOPYRIDO[1',2':4,5]PYRAZINO[2,1-B][1,3]OXAZEPINE-10-CARBOXAMIDE), were measured by characterizing API dissolution from a constant surface area. Approximately 150 mg of the drug substance was compressed at 1500 psi for approximately 3 seconds using a hydraulic press (Carver Press, Fred Carver, NJ, USA). The compressed drug substance formed a flat disk (surface area~0.49 cm²), which was mounted onto a dissolution apparatus (VanKel Industries Inc., Edison, N.J., VK7000, W1120A-0288). The rotating disk (100 rpm) was then lowered into the dissolution medium (500 mL of 0.01N HCl) which was equilibrated to 37±1° C. Samples were pulled at pre-determined time points and drug concentrations were measured using an appropriate UPLC-UV method. The intrinsic dissolution rate constant (K) was calculated using the following equation:

$$C = \frac{KA}{V}t$$

Where C is the concentration of the active at time t, A is the surface area of the tablet (~0.49 cm$^2$) and V is the volume of the media (500 mL). Note that the term active as used herein refers to the parent molecule, whose structure is shared by both Formula I and Formula II.

Figure 5:
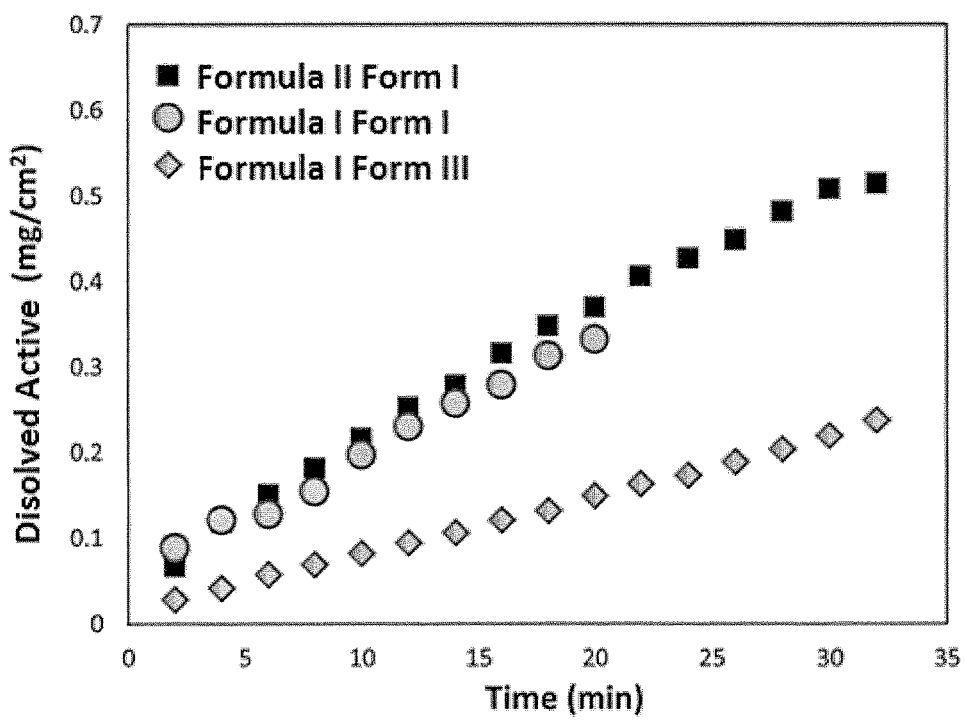
FIG. 5: Dissolution profiles of Formula I Form I, Formula I Form III, and Formula II Form I.

The dissolution profiles can be found in FIG. 5.

Solubility

The solubility of the sodium form of the present invention and the free acid, (2R,5S,13aR)-8-hydroxy-7,9-dioxo-N-(2,4,6-trifluorobenzyl)-2,3,4,5,7,9,13,13a-octahydro-2,5-methanopyrido[1',2':4,5]pyrazino[2,1-b][1,3]oxazepine-10-carboxamide Form III in biorelevant media was determined at room temperature as a function of time. Solubility was determined in the following biorelevant media: 0.1 mM Fasted-State Simulated Gastric Fluid (FaSSGF) pH 1.6 (0.08 mM taurocholate, 0.02 mM lecithin, 34.2 mM NaCl); 18.75 mM Fed-State Simulated Intestinal Fluid (FeSSIF) pH 5 (15 mM taurocholate, 3.75 mM lecithin, 0.12 M NaCl); and 3.75 mM Fasted-State Simulated Intestinal Fluid (FaS-SIF) pH 5 (3 mM taurocholate, 0.75 mM lecithin, 0.10 M NaCl). Approximately 20 mg of the drug substance was mixed on a magnetic stir-plate in 50 mL of biorelevant media. Samples (~1 mL) were pulled every 5-10 min for 2 hours. The samples were immediately filtered/centrifuged for 10 min in a Spin-X tube equipped with a 0.45 µm nylon filter. The resulting filtrate was analyzed using an appropriate UPLC-UV method.

Figure 6:
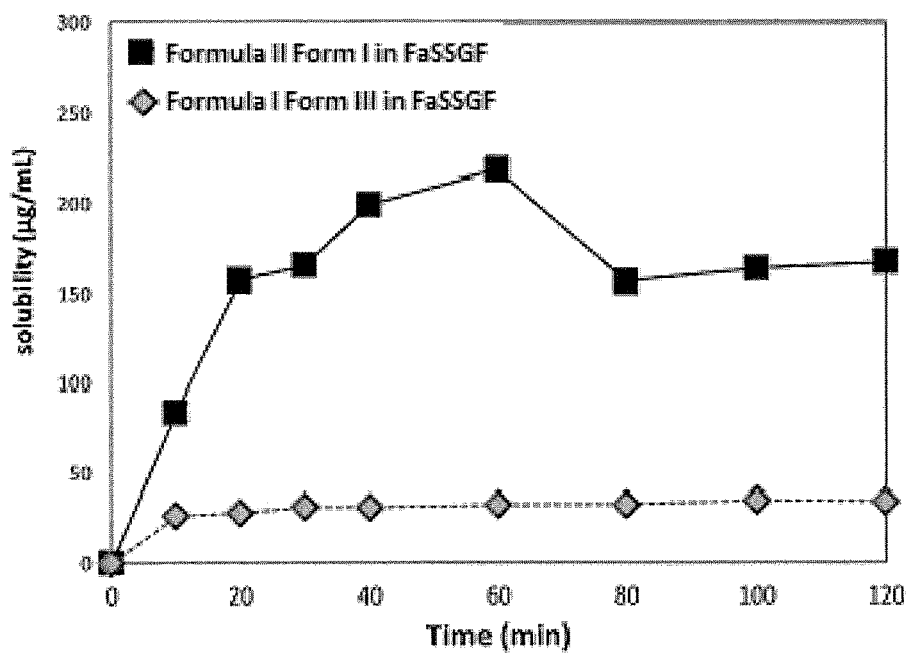
FIG. 6: Solubility profiles of Formula I Form III and Formula II Form I in Fasted-State Simulated Gastric Fluid (FaSSGF).
Figure 7:
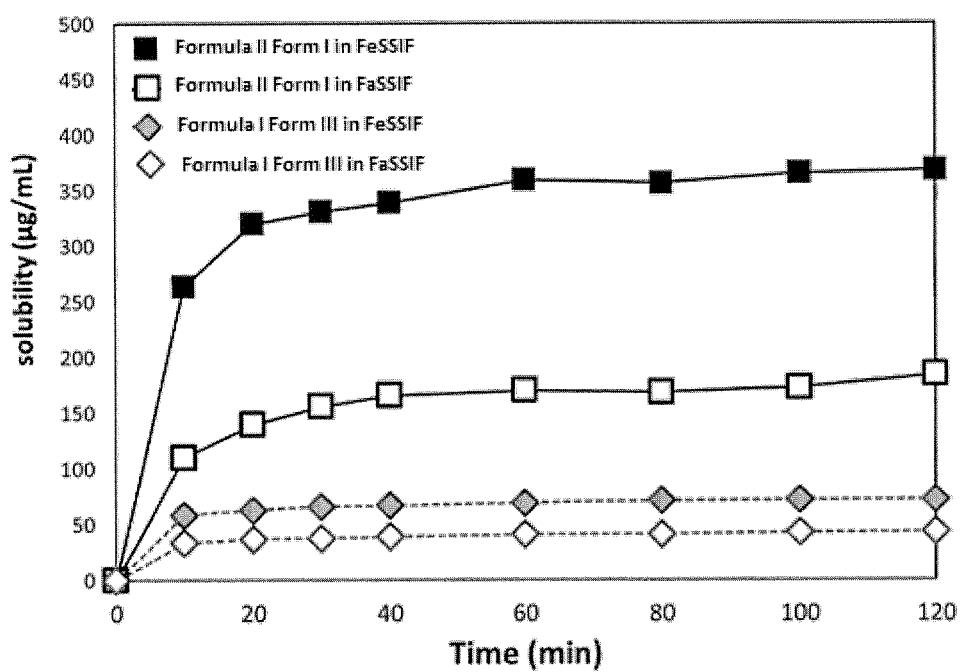
FIG. 7: Solubility profiles of Formula I Form III and Formula II Form I in Fed-State Simulated Intestinal Fluid (FeSSIF) and Fasted-State Simulated Intestinal Fluid (FaSSIF).

The solubility profiles in FaSSGF can be found in FIG. 6. The solubility profiles in FeSSIF and FaSSIF can be found in FIG. 7.

Bioavailability

The bioavailability of sodium (2R,5S,13aR)-7,9-dioxo-10-((2,4,6-trifluorobenzyl)carbamoyl)-2,3,4,5,7,9,13,13a-octahydro-2,5-methanopyrido[1',2':4,5]pyrazino[2,1-b][1,3]oxazepin-8-olate (Formula II) Form I was compared to the bioavailability of (2R,5S,13aR)-8-hydroxy-7,9-dioxo-N-(2,4,6-trifluorobenzyl)-2,3,4,5,7,9,13,13a-octahydro-2,5-methanopyrido[1',2':4,5]pyrazino[2,1-b][1,3]oxazepine-10-carboxamide (Formula I) Form III.

Each dosing group consisted of 6 male, non-naïve purebred beagle dogs. At dosing, the animals weighed between 10 to 13 kg. The animals were fasted overnight prior to dose administration and up to 4 hr after dosing. Each subject was pre-treated with pentagastrin (6 µg/kg) and dosed 30 minutes later with a single 25 mg strength tablet of Formula II Form I or Formula I Form III. Each subject was given 10 mL of water to aid in swallowing.

Serial venous blood samples (approximately 1 mL each) were taken from each animal at 0, 0.250, 0.483, 0.583, 0.750, 1.00, 1.50, 2.00, 4.00, 8.00, 12.0, and 24.0 hours after dosing. The blood samples were collected into Vacutainer™ tubes containing EDTA-K2 as the anti-coagulant and were immediately placed on wet ice pending centrifugation for plasma. An LC/MS/MS method was used to measure the concentration of the test compound in plasma. An aliquot of 100 µL of each plasma sample was added to a clean 96 well plate, and 400 µL of cold acetonitrile/internal standard solution (ACN)/(ISTD) was added. After protein precipitation, an aliquot of 110 µL of the supernatant was transferred to a clean 96-well plate and diluted with 300 µL of water. An aliquot of 25 µL of the above solution was injected into a TSQ Quantum Ultra LC/MS/MS system utilizing a Hypersil Gold C$_{18}$ HPLC column (50×3.0 mm, 5 µm; Thermo-Hypersil Part #25105-053030). An Agilent 1200 series binary pump (P/N G1312A Bin Pump) was used for elution and separation, and an HTS Pal autosampler (LEAP Technologies, Carrboro, N.C.) was used for sample injection. A TSQ Quantum Ultra triple quadrupole mass spectrometer was utilized in selective reaction monitoring mode (Thermo Finnigan, San Jose, Calif.). Liquid chromatography was performed using two mobile phases: mobile phase A contained 1% acetonitrile in 2.5 mM ammonium formate aqueous solution with pH of 3.0, and mobile phase B contained 90% acetonitrile in 10 mM ammonium formate with pH of 4.6. Non-compartmental pharmacokinetic analysis was performed on the plasma concentration-time data. The resulting data are shown in Table 3: F (%) refers to oral bioavailability; AUC refers to area under the curve and is a measure of total plasma exposure of the indicated compound; C$_{max}$ refers to the peak plasma concentration of the compound after administration.

TABLE 3

Bioavailability of sodium (2R,5S,13aR)-7,9-dioxo-10-((2,4,6-trifluorobenzyl)carbamoyl)-2,3,4,5,7,9,13,13a-octahydro-2,5-methanopyrido[1',2':4,5]pyrazino[2,1-b][1,3]oxazepin-8-olate Form I and (2R,5S,13aR)-8-hydroxy-7,9-dioxo-N-(2,4,6-trifluorobenzyl)-2,3,4,5,7,9,13,13a-octahydro-2,5-methanopyrido[1',2':4,5]pyrazino[2,1-b][1,3]oxazepine-10-carboxamide Form III.

| Form | Formulation | % F | AUC$_{last}$ (uM × hr) | C$_{max}$ (uM) |
|---|---|---|---|---|
| Formula I Form III | Dry Granulation[1] | 10 ± 6 | 27 ± 13 | 6 ± 2 |
| Formula II Form I | Dry Granulation[2] | 28 ± 7 | 71 ± 16 | 13 ± 1 |

[1]Tablet: 30% active, 56% microcrystalline cellulose, 13% croscarmellose sodium, 1% magnesium stearate
[2]Tablet: 30% active, 56% microcrystalline cellulose, 13% croscarmellose sodium, 1% magnesium stearate Stability The stability of sodium (2R,5S,13aR)-7,9-dioxo-10-((2,4,6-trifluorobenzyl)carbamoyl)-2,3,4,5,7,9,13,13a-octahydro-2,5-methanopyrido[1',2':4,5]pyrazino[2,1-b][1,3]oxazepin-8-olate Form I was tested. As seen in Table 4, below, the compound is stable after four weeks of storage under accelerated conditions. In Table 5, AN refers to area normalization and is the relative peak area of the active with respect to other impurities and components contained in the sample. LS refers to labile strength and is the amount of active present relative to the theoretical amount.

TABLE 4

Stability of sodium (2R,5S,13aR)-7,9-dioxo-10-((2,4,6-trifluorobenzyl)carbamoyl)-2,3,4,5,7,9,13,13a-octahydro-2,5-methanopyrido[1',2':4,5]pyrazino[2,1-b][1,3]oxazepin-8-olate Form I

| Storage Conditions | Storage Time (weeks) | % AN | % LS |
|---|---|---|---|
| Starting material | 0 | 94.4 ± 0.1 | 99.8 ± 0.1 |
| 40° C. (closed) | 1 | 95.2 ± 0.3 | 108.0 ± 0.2 |
|  | 2 | 94.4 ± 0.1 | 102.4 ± 0.1 |
|  | 4 | 94.4 ± 0.0 | 97.0 ± 0.0 |
| 40° C./75% RH (open) | 1 | 94.9 ± 0.1 | 103.3 ± 6.9 |
|  | 2 | 94.4 ± 0.0 | 108.5 ± 0.4 |
|  | 4 | 94.4 ± 0.0 | 102.9 ± 0.1 |
| 25° C./60% RH (open) | 1 | 95.0 ± 0.2 | 104.8 ± 0.1 |
|  | 2 | 94.4 ± 0.1 | 101.6 ± 0.1 |
|  | 4 | 94.4 ± 0.0 | 103.0 ± 0.8 |

Each of the references including all patents, patent applications and publications cited in the present application is incorporated herein by reference in its entirety, as if each of them is individually incorporated. Further, it would be appreciated that, in the above teaching of invention, the skilled in the art could make certain changes or modifications to the invention, and these equivalents would still be within the scope of the invention defined by the appended claims of the application. Each of the references including all patents, patent applications and publications cited in the present application is incorporated herein by reference in its entirety, as if each of them is individually incorporated. Further, it would be appreciated that, in the above teaching of invention, the skilled in the art could make certain changes or modifications to the invention, and these equivalents would still be within the scope of the invention defined by the appended claims of the application.

What is claimed:

1. A compound of Formula II:

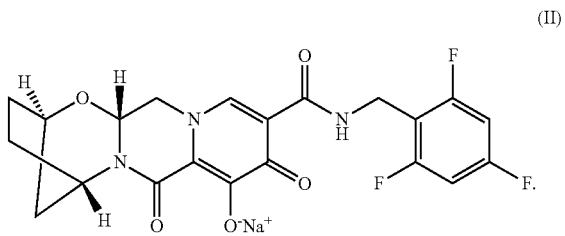

(II)

2. The compound of claim 1, characterized by being crystalline.

3. The compound of claim 2, characterized by an x-ray powder diffraction (XRPD) pattern having peaks at about 5.5°, 16.1°, and 23.3° 2-θ±0.2° 2-θ.

4. The compound of claim 3, wherein the x-ray powder diffraction (XRPD) pattern has further peaks at about 22.1°, and 28.5° 2-θ±0.2° 2-θ.

5. The compound of claim 4, wherein the x-ray powder diffraction (XRPD) pattern has further peaks at about 22.5 and 19.5° 2-θ±0.2° 2-θ.

6. The compound of claim 5, wherein the x-ray powder diffraction (XRPD) pattern has further peaks at about 26.6° and 17.9° 2-θ±0.2° 2-θ.

7. The compound of claim 2, characterized by an x-ray powder diffraction (XRPD) pattern substantially as set forth in FIG. 1.

8. The compound of claim 2, characterized by differential scanning calorimetry (DSC) pattern substantially as set forth in FIG. 2.

9. The compound of claim 2, characterized by a dynamic vapor sorption (DVS) pattern substantially as set forth in FIG. 4.

10. The compound of any one of claims 1 to 9, characterized in being partially or fully hydrated.

11. The compound of any one of claims 1 to 9, characterized in being anhydrous or essentially anhydrous.

12. A pharmaceutical composition comprising a therapeutically effective amount of a compound of any one of claims 1 to 9, and a pharmaceutically acceptable carrier or excipient.

13. The pharmaceutical composition of claim 12, further comprising one to three additional therapeutic agents.

14. The pharmaceutical composition of claim 13, wherein the additional therapeutic agents are each anti-HIV drugs.

15. The pharmaceutical composition of claim 13, wherein the additional therapeutic agents are each independently selected from the group consisting of HIV protease inhibitors, HIV non-nucleoside inhibitors of reverse transcriptase, HIV nucleoside inhibitors of reverse transcriptase, HIV nucleotide inhibitors of reverse transcriptase, pharmacokinetic enhancers and other drugs for treating HIV.

16. The pharmaceutical composition of claim 13, wherein one of the one to three additional therapeutic agents is an HIV nucleoside inhibitor of reverse transcriptase.

17. The pharmaceutical composition of claim 12, further comprising tenofovir disoproxil fumarate and emtricitabine.

18. The pharmaceutical composition of claim 12, further comprising tenofovir alafenamide and emtricitabine.

19. The pharmaceutical composition of claim 12, further comprising tenofovir alafenamide hemifumarate and emtricitabine.

20. The pharmaceutical composition of claim 12, wherein the pharmaceutical composition is in an oral unit dosage form.

21. The pharmaceutical composition of claim 20, wherein the unit dosage form is a tablet.

22. A pharmaceutical composition comprising a therapeutically effective amount of a compound of any one of claims 1 to 9, and a pharmaceutically acceptable carrier or excipient, the composition further comprising one to three additional therapeutic agents, wherein each of the one to three additional therapeutic agents is independently an HIV nucleoside inhibitor of reverse transcriptase or an HIV nucleotide inhibitor of reverse transcriptase.

23. The pharmaceutical composition of claim 22, wherein the pharmaceutical composition is in an oral unit dosage form.

24. The pharmaceutical composition of claim 22, wherein the pharmaceutical composition is a tablet.

25. The pharmaceutical composition of claim 12, further comprising tenofovir alafenamide fumarate and emtricitabine.

26. The pharmaceutical composition of claim 12, further comprising tenofovir alafenamide hemifumarate and emtricitabine.

* * * * *